US010945938B2

(12) United States Patent
Yamasaki et al.

(10) Patent No.: US 10,945,938 B2
(45) Date of Patent: Mar. 16, 2021

(54) LACTONE-CONTAINING COMPOSITIONS FOR MALODOR ELIMINATION

(71) Applicant: Takasago International Corporation, Tokyo (JP)

(72) Inventors: Akiko Yamasaki, Cliffside Park, NJ (US); John D. Zanone, Towaco, NJ (US); Michael John Munroe, Piermont, NY (US)

(73) Assignee: Takasago International Corporation, Tokyo (JP)

(*) Notice: Subject to any disclaimer, the term of this patent is extended or adjusted under 35 U.S.C. 154(b) by 0 days.

(21) Appl. No.: 14/791,138

(22) Filed: Jul. 2, 2015

(65) Prior Publication Data
US 2016/0000679 A1 Jan. 7, 2016

Related U.S. Application Data

(60) Provisional application No. 62/020,908, filed on Jul. 3, 2014, provisional application No. 62/020,915, filed on Jul. 3, 2014.

(51) Int. Cl.
C11D 3/50 (2006.01)
A61K 8/49 (2006.01)
A61Q 11/00 (2006.01)
A61Q 15/00 (2006.01)
A61Q 5/02 (2006.01)
A61Q 13/00 (2006.01)
A61Q 19/10 (2006.01)
A61K 8/34 (2006.01)
A61K 8/35 (2006.01)
A61K 8/37 (2006.01)
A61Q 5/12 (2006.01)
A61Q 5/06 (2006.01)
C11D 3/20 (2006.01)
A23C 9/00 (2006.01)
A61K 8/92 (2006.01)
A61K 8/365 (2006.01)
A61Q 11/02 (2006.01)
C11D 3/00 (2006.01)
C11D 7/26 (2006.01)

(52) U.S. Cl.
CPC ............ A61K 8/4973 (2013.01); A23C 9/005 (2013.01); A61K 8/34 (2013.01); A61K 8/347 (2013.01); A61K 8/35 (2013.01); A61K 8/365 (2013.01); A61K 8/37 (2013.01); A61K 8/498 (2013.01); A61K 8/922 (2013.01); A61Q 5/02 (2013.01); A61Q 5/06 (2013.01); A61Q 5/12 (2013.01); A61Q 11/00 (2013.01); A61Q 11/02 (2013.01); A61Q 13/00 (2013.01); A61Q 15/00 (2013.01); A61Q 19/10 (2013.01); C11D 3/0068 (2013.01); C11D 3/2096 (2013.01); C11D 7/267 (2013.01); A23V 2002/00 (2013.01)

(58) Field of Classification Search
CPC .... A61K 2300/00; A61K 8/347; A61Q 15/00; A61Q 11/00; A61Q 13/00; A61Q 5/02; A61Q 19/10; A61Q 5/12; C11D 3/0068
See application file for complete search history.

(56) References Cited

U.S. PATENT DOCUMENTS

| 3,914,227 A | 10/1975 | Pittet et al. |
| 4,906,488 A | 3/1990 | Pera |
| 5,464,824 A | 11/1995 | Gaudin |
| 5,580,545 A | 12/1996 | Washino et al. |
| 5,589,158 A | 12/1996 | Mankoo |
| 5,739,100 A | 4/1998 | Horino et al. |
| 6,471,946 B1 | 10/2002 | Takatsuka et al. |
| 6,491,896 B1 | 12/2002 | Rajaiah et al. |
| 6,495,176 B1 | 12/2002 | McGenity et al. |
| 6,723,305 B2 | 4/2004 | DePierro et al. |
| 6,868,923 B2 | 3/2005 | Cunningham et al. |
| 7,300,645 B2 | 11/2007 | Takatsuka et al. |
| 7,332,462 B2 | 2/2008 | McGee et al. |
| 7,465,697 B1 | 12/2008 | DeAth |
| 8,007,771 B2 | 8/2011 | Ramji et al. |
| 2002/0064505 A1* | 5/2002 | Rosenberg ............. A01N 31/02 424/49 |
| 2004/0037792 A1* | 2/2004 | Hiramoto ................. A23G 3/36 424/65 |
| 2004/0141927 A1 | 7/2004 | Johnson et al. |
| 2006/0002876 A1 | 1/2006 | Cahen |
| 2006/0153959 A1 | 7/2006 | Behan et al. |

(Continued)

FOREIGN PATENT DOCUMENTS

| CN | 106535865 A | 3/2017 |
| EP | 0404470 A1 | 12/1990 |

(Continued)

OTHER PUBLICATIONS

PubChem. Dihydrocoumarin. Date retrieved: Apr. 5, 2017. <https://pubchem.ncbi.nlm.nih.gov/compound/dihydrocoumarin#section=Top>.*
U.S. Appl. No. 12/615,157, filed Nov. 9, 2009.
U.S. Appl. No. 12/615,157, Jun. 7, 2012 Non-Final Office Action.
U.S. Appl. No. 12/615,157, Aug. 30, 2012 Response to Non-Final Office Action.
U.S. Appl. No. 12/615,157, Nov. 26, 2012 Final Office Action.
U.S. Appl. No. 12/615,157, May 28, 2013 Amendment and Request for Continued Examination.

(Continued)

Primary Examiner — Tracy Liu
(74) Attorney, Agent, or Firm — Baker Botts L.L.P.

(57) ABSTRACT

The presently disclosed subject matter provides lactone-containing malodor eliminating compositions that ameliorate undesirable malodor, e.g., undesirable malodor due to presence of sulfur- or amine-containing compounds. The presently disclosed compositions can be added to a variety of products, including, but not limited to, foods, beverages, toothpastes, mouthwashes and other orally consumable products.

11 Claims, 1 Drawing Sheet

(56) References Cited

U.S. PATENT DOCUMENTS

| | | | |
|---|---|---|---|
| 2006/0165622 A1 | 7/2006 | Hiramoto et al. | |
| 2006/0222615 A1 | 10/2006 | Kuroda et al. | |
| 2007/0149424 A1 | 6/2007 | Warr et al. | |
| 2008/0008665 A1* | 1/2008 | Ramji | A61K 8/4973 424/48 |
| 2008/0008667 A1 | 1/2008 | Hoke et al. | |
| 2008/0085246 A1 | 4/2008 | Rabenhorst et al. | |
| 2008/0247966 A1 | 10/2008 | Natsch et al. | |
| 2008/0311054 A1 | 12/2008 | Natsch et al. | |
| 2009/0010958 A1* | 1/2009 | Pinney | A61K 8/33 424/195.18 |
| 2009/0087401 A1* | 4/2009 | Hiramoto | A61K 8/347 424/76.1 |
| 2009/0148568 A1* | 6/2009 | Kawamura | A23G 3/36 426/89 |
| 2009/0271936 A1* | 11/2009 | Walanski | A61B 5/0088 15/105 |
| 2009/0317536 A1 | 12/2009 | Cambeen et al. | |
| 2010/0028288 A1 | 2/2010 | Tranzeat et al. | |
| 2012/0052031 A1 | 3/2012 | Troccaz et al. | |
| 2013/0136713 A1* | 5/2013 | Terada | A61L 9/01 424/76.1 |
| 2015/0104398 A1 | 4/2015 | Chin et al. | |

FOREIGN PATENT DOCUMENTS

| | | |
|---|---|---|
| EP | 1 561 476 A1 | 8/2005 |
| JP | 10-158257 A | 6/1998 |
| JP | 2003-190264 A | 7/2003 |
| JP | 2004-155681 A | 6/2004 |
| JP | 2005-013138 | 1/2005 |
| JP | 2005-75821 A | 3/2005 |
| JP | 2005-187394 A | 7/2005 |
| JP | 2006-121958 A | 5/2006 |
| JP | 2007-99782 A | 4/2007 |
| JP | 2009-179711 A | 8/2009 |
| JP | 2010-254898 A | 11/2010 |
| WO | WO 2005/110499 A1 | 11/2005 |
| WO | WO 2007/007978 A1 | 1/2007 |
| WO | WO 2007/071085 A1 | 6/2007 |
| WO | WO 2008/005548 A2 | 1/2008 |
| WO | WO 2008/026140 A2 | 3/2008 |
| WO | WO 2008/135746 A2 | 11/2008 |
| WO | WO 2010/146556 A2 | 12/2010 |

OTHER PUBLICATIONS

U.S. Appl. No. 12/615,157, Jun. 24, 2013 Non-Final Office Action.
U.S. Appl. No. 12/615,157, Sep. 24, 2013 Response to Non-Final Office Action.
U.S. Appl. No. 12/615,157, Feb. 28, 2014 Final Office Action.
U.S. Appl. No. 12/615,157, Aug. 28, 2014 Amendment and Request for Continued.
U.S. Appl. No. 12/615,157, Apr. 13, 2015 Non-Final Office Action.
U.S. Appl. No. 12/615,157, Sep. 17, 2015 Applicant Initiated Interview Summary.
U.S. Appl. No. 12/615,157, Oct. 13, 2015 Response to Non-Final Office Action.
"Damascenone", SciFinder. CAS Registry Number: 23726-93-4:_ Damascenone.
Fadel, "Comparison Studies on Leaf Oils of Egyptian Citrus Varieties" Journal of Islamic Academy of Sciences 4:3, 196-199, 1991.
Honda, et al. "Detergent with anticorrosive function comprises soapberry peel and glycerol in a specific weight ratio" CN103142430 (2013) English Abstract.
Liu, "Formula of plum extract-containing casing flavor for tobacco" CN102150941 (2011) English Abstract.
U.S. Appl. No. 12/615,157, Jan. 19, 2016 Notice of Allowance.
Annex to the Invitation to Pay Additional Fees dated Jan. 14, 2016 in International Application No. PCT/IB2015/001677.
International Search Report and Written Opinion dated Mar. 23, 2016 in International Application No. PCT/IB2015/001677.
U.S. Appl. No. 12/615,157, Apr. 19, 2016 Issue Fee Payment.

* cited by examiner

LACTONE-CONTAINING COMPOSITIONS FOR MALODOR ELIMINATION

CROSS-REFERENCE TO RELATED APPLICATIONS

This application claims benefit under 35 U.S.C. § 119(e) to U.S. Provisional Application Ser. No. 62/020,908, filed on Jul. 3, 2014, and U.S. Provisional Application Ser. No. 62/020,915, filed on Jul. 3, 2014, priority to each of which is claimed, and each of which is incorporated by reference in its entirety.

FIELD OF THE INVENTION

The present disclosed subject matter relates to compositions that ameliorate undesirable malodor, e.g., undesirable malodor due to the presence of sulfur- and amine-containing compounds. The presently disclosed compositions can be added to a variety of products, including, but not limited to, foods, beverages, toothpastes, mouthwashes, other orally consumable products, animal care products, cleaning products, and deodorizing products.

BACKGROUND OF THE INVENTION

It is known in the art that various materials may temporarily alleviate oral malodor, which imparts undesirable tastes to orally consumed products. These materials include, for example, antibacterial agents, natural extracts with or without an enzyme component, antioxidants, chelating agents, and fragrance and flavor materials. Other substances, which are known to control oral malodor, include quaternary ammonium compounds, triclosan, baking soda, cetylpyridinium chloride, cyclohexidine, zinc salts, stannous salts, antibacterial flavor materials, essential oils, and natural extracts, e.g., polyphenol.

These materials can provide an oral malodor suppression effect in various ways when applied to the oral cavity. For example, the suppression effect may be due to the prevention of malodor generation, by chemically reacting with malodor materials, or by simply masking the malodor. U.S. Patent Publication No. 2008/0311054 describes oral malodor counteracting compositions using unsaturated alkanoic acid esters. These active ingredients have been shown to inhibit the enzymes that produce oral bacteria. Similarly, U.S. Patent Publication No. 2008/0247966 relates to an oral malodor counteracting composition that is based on bacterial enzyme inhibition.

Other substances are known in the art that attempt to reduce malodor. For example, U.S. Pat. No. 8,007,771 discloses protectant components that prevent generation of malodor and off-taste in an oral care composition. Additionally, U.S. Patent Publication No. 2008/0085246 teaches a method of inhibiting the growth of micro-organisms that cause bad breath.

Malodor counteractancy or counteracting (MOC) methods are known to neutralize or mask malodors. For example, U.S. Patent Publication No. 2010/0028288 and International Patent Publication No. WO 2008/026140 disclose MOC compositions comprising at least one nitrile material in combination with another fragrance material for use in consumer products. U.S. Patent Publication No. 2012/0052031 and International Patent Publication No. WO 2010/8146556 disclose MOC compositions capable of at least reducing sweat malodor. These compositions contain at least one MOC ingredient having a malodor inhibition coefficient of at least 25% against malodor generated by *Staphylococcus haemolyticus* enzymatic activity in the medium. International Patent Publication No. WO 2005/110499 discloses an odor-reducing composition for counteracting malodorous amines comprising at least one odor-reducing material selected from the group consisting of phenyl ethyl methyl ether, cyprisate, camonal and paracresyl methyl ether.

International Patent Publication No. WO 2007/071085 describes oral malodor counteracting compositions that include esterified fumarates, which are said to chemically bind to malodor molecules. However, these counteracting compositions are not practical and common flavor materials can be expensive and difficult to obtain.

The various materials used in the prior art can cause unpleasant effects including astringency or a metallic taste, or are unstable in an orally consumable product. Compositions that merely mask malodor only reduce malodor perception; they do not eliminate the malodor, which persists in the oral cavity. Therefore, there remains a need for improved compositions that can reduce malodor materials in orally consumed products.

SUMMARY OF THE INVENTION

The presently disclosed subject matter provides malodor eliminating compositions that provide efficient malodor elimination, e.g., malodor caused by sulfur-containing and amine-containing compounds.

In one embodiment, the presently disclosed subject matter provides a malodor eliminating composition comprising at least one lactone. In one embodiment, the presently disclosed subject matter provides a malodor eliminating composition comprising at least one lactone and at least one phenolic compound.

In certain embodiments, the at least one lactone is selected from the group consisting of, but not limited to, *angelica* lactone alpha, *angelica* lactone beta, mint lactone, δ-2-decenolactone, 2(5H) furanone, and combinations thereof.

In certain embodiments, the at least one phenolic compound is selected from the group consisting of, but not limited to, eugenol, Hotact® VBE, Hotact® VEE, benzyl salicylate, methyl salicylate, raspberry ketone, thymol, vanillin, ethyl vanillin, vanitrope, and combinations thereof.

In one embodiment, the malodor eliminating composition of the presently disclosed subject matter further comprises a malodor masking compound. The malodor masking compound is selected from the group consisting of, but not limited to, menthol, anisyl acetate, ethyl acetate, phenethyl alcohol, ethyl 2-methyl butyrate, ethyl butyrate, propylene glycol, citrus oils, peppermint oil, spearmint oil, oil of wintergreen, cinnamon, and ginger, and combinations thereof.

In one embodiment, the malodor eliminating composition of the presently disclosed subject matter further comprises a diol solvent. The diol solvent is selected from the group consisting of, but not limited to, 3-(1-menthoxy)propane-1, 2-diol, p-menthane-3,8-diol, propylene glycol, diethylene glycol, dipropylene glycol, and combinations thereof.

The presently disclosed subject matter also provides an oral care end product comprising the above-described malodor eliminating composition.

DETAILED DESCRIPTION

Figure 1:
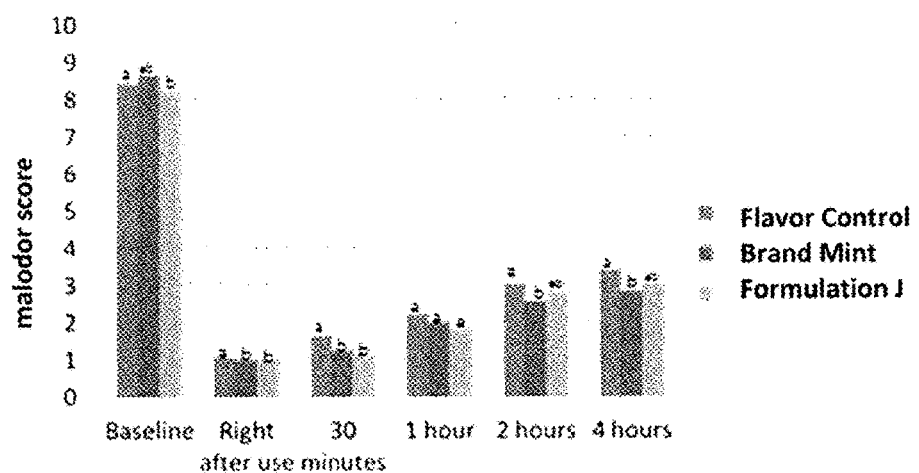
FIG. 1: Hedonic scale results from the clinical study evaluating the mint toothpaste of Formulation J. Statistics were run between each treatment group at each time point. Bars with the same letter are not significantly different (p<0.05).

As used herein, "malodor eliminating" or "malodor suppression" refers to at least partial removal of malodor-causing materials as opposed to simply masking (i.e., covering up) of the perception of a malodor.

As used herein, a "malodor eliminating composition" refers to a composition or product that facilitates at least partial removal of malodor-causing materials, e.g., via chemical reaction(s) with the malodor-causing constituent, as opposed to a composition that simply masks (i.e., covers up) the perception of a malodor. In certain embodiments, malodor-causing constituents react with at least one of the components or ingredients of the malodor eliminating composition to form at least one new compound that is more pleasing, or at least less displeasing. In certain embodiments, at least one of the components or ingredients of the malodor eliminating compositions possesses specific chemical functional groups that are prone to react with a variety of malodor-causing constituents, especially malodor-causing constituents, including, but not limited to, thiols and amines.

As used herein, a "malodor masking compound" refers to a compound that masks the perception of a malodor, thereby providing a pleasing perception to the consumer of an orally consumed product, or otherwise rendering the product to which it is applied (e.g., an orally consumed consumer product) more appealing, or less displeasing. A malodor masking compound does not chemically interact with the malodor-causing constituent to create a new compound.

As used herein, a "consumer product" or "end product" refers to a product comprising the presently disclosed composition that is in a form ready for use by consumers for the marketed indication. For example, and without limitation, a mouthwash or a mouthrinse consumer product refers to a consumer product that is indicated for oral and/or buccal use for improving oral hygiene (e.g., to ameliorate halitosis and/or dental plaque). A wider example of products is included further below. Such products may be in a form suitable for a subject's oral cavity, sublabial, sublingual, and/or buccal administration (e.g., as a gargle or rinse). Such products may also be in a form for oral consumption.

As used herein, a "solvent suitable for use in a consumer product" is a solvent that, when combined with other components of an end product, will not render the end product unfit for its intended use. For example and without limitation, a solvent suitable for use in a mouthwash or mouthrinse must be one that does not compromise the ability of the end product to be orally consumed as indicated (e.g., gargled, rinsed and/or swallowed).

As used herein, "ppm" means parts-per-million and is a weight relative parameter. A part-per-million is a microgram per gram, such that a component that is present at 1 ppm is present at 1 micrograms of the specific component per 1 gram of the aggregate mixture or 1 milligram in 1 liter of water.

As used herein, "synergy," "synergistically," or "synergistic effect" refers to an effect produced by two or more individual components in which the total effect produced by these components, when utilized in combination, is greater than the sum of the individual effects of each component acting alone.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value.

Malodor Eliminating Compositions

The presently disclosed subject matter provides malodor eliminating compositions comprising at least one lactone. The presently disclosed subject matter also provides malodor eliminating compositions comprising at least one lactone and at least one phenolic compound.

The combination of at least one lactone and at least one phenolic compound provides measurable benefits for the suppression and/or elimination of malodor. In certain embodiments, the combination provides surprising and unexpected malodor suppression and malodor elimination. For example, the combination of at least one lactone and at least one phenolic compound provides more malodor suppression or elimination than the mere additive effect of each of the compounds alone.

Lactones

In accordance with the presently disclosed subject matter, the presently disclosed compositions comprise at least one lactone. In certain embodiments, the lactone comprises a 3-, 4-, 5-, 6-, 7-, or 8-membered lactone ring. In certain embodiments, the lactone comprises a 5-membered lactone ring with or without unsaturated bond(s). In certain embodiments, the lactone comprises a 5-membered lactone ring including at least one unsaturated bond. In certain embodiments, the lactone comprises a 5-membered lactone ring including at least one unsaturated bond, which can have a chemical structure represented by Formula 1a or Formula 1b, where $R_1$, $R_2$, $R_3$, and $R_4$ can be independently selected from the group consisting of hydrogen, hydroxyl, and aliphatic $C_1$-$C_8$, wherein the aliphatic $C_1$-$C_8$ can be straight-chained or branched and can independently be saturated or unsaturated. In certain embodiments, $R_2$ and $R_3$ can alternatively be taken together to form a 6-membered carbocyclic ring, which can be saturated, unsaturated, or aromatic, and can optionally be further substituted by one or more aliphatic $C_1$-$C_8$ substituents, which can be straight-chained or branched and can independently be saturated or unsaturated. In certain embodiments, $R_1$ is not a hydroxyl group. In certain embodiments, $R_2$ is not a hydroxyl group.

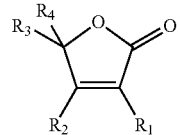

Formula 1a

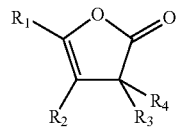

Formula 1b

Examples of lactones comprising a 5-membered lactone ring having at least one unsaturated bond include, but are not limited to, *angelica* lactone alpha, *angelica* lactone beta, mint lactone, 5,5-dimethyl-2(5H)-furanone, 5-ethyl-2(5H)-furanone, 5-pentyl-2(5H)-furanone, 5-hexyl-2(5H)-furanone, 5-pentyl-2(3H)-furanone, 4-methyl-3-pentyl-2(5H)-furanone, and 2(5H)-furanone. In certain embodiments, the lactone is *angelica* lactone alpha. In other embodiments, the lactone is *angelica* lactone beta. In certain embodiments, *angelica* lactone alpha and *angelica* lactone beta are used because they have a neutral odor on their own (either separately or together). As they have little odor, they are able to be used, either separately or together, at any amount without impacting the odor or taste of a composition in which they are added.

In certain embodiments, the lactone comprises a 5-membered lactone ring without any unsaturated bonds. Examples of such lactones include, but are not limited to, butyrolactone gamma, valerolactone gamma, hexalactone gamma, heptalactone gamma, octalactone gamma, undecalactone gamma, decalactone gamma, dihydrojasmone lactone, and dihydromintlactone (also called Natactone™).

Additionally and alternatively, the lactone comprises a 6-membered lactone ring with or without unsaturated bond(s). In certain embodiments, the lactone comprises a 6-membered lactone ring including at least one unsaturated bond. The lactone comprises a 6-membered lactone ring having at least one unsaturated bond can have a chemical structure represented by Formula 2a, 2b, or 2c, where $R_5$, $R_6$, $R_7$, $R_8$, $R_9$, and $R_{10}$ can be independently selected from the group consisting of hydrogen, hydroxyl, and aliphatic $C_1$-$C_8$, wherein the aliphatic $C_1$-$C_8$ can be straight-chained or branched and can independently be saturated or unsaturated. In some embodiments of Formula 2a, $R_8$ and $R_9$ can be taken together to form a 6-membered carbocyclic ring, which can be saturated, unsaturated, or aromatic, and which can optionally be further substituted by one or more aliphatic $C_1$-$C_8$ substituents, which can be straight-chained or branched and can independently be saturated or unsaturated.

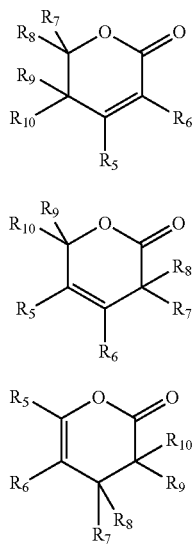

Formula 2a

Formula 2b

Formula 2c

Examples of lactones comprising a 6-membered lactone ring having at least one unsaturated bond include, but are not limited to, δ-2-decenolactone, coumarin, and 6-methylcoumarin.

In other embodiments, the lactone includes a 6-membered lactone ring without any unsaturated bonds. Examples of lactones including a 6-membered lactone ring without any unsaturated bonds include, but are not limited to, decalactone delta, dodecalactone delta, and cyclohexyl lactone.

In certain embodiments, the presently disclosed lactone (e.g., alpha, beta-unsaturated lactone) can react with nucleophilic malodor materials, e.g., thiols and amines, via the Michael addition reaction (as shown in Schemes 1 and 2), to eliminate malodor.

Scheme 1

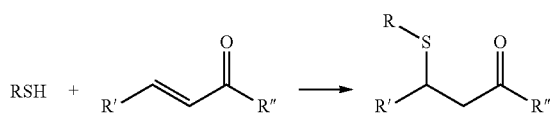

Scheme 2

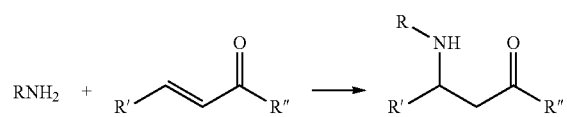

In an alternative embodiment, a lactone can react with malodor materials via a ring-opening reaction.

Scheme 3 demonstrates possible reaction products formed by the Michael addition reaction (Scheme 3a) and the ring opening reaction (Scheme 3b).

Scheme 3a

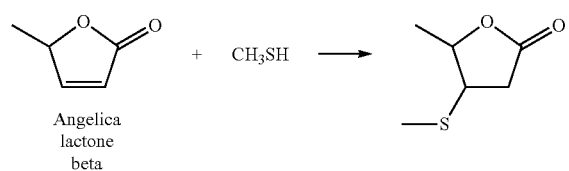

Angelica lactone beta

Scheme 3b

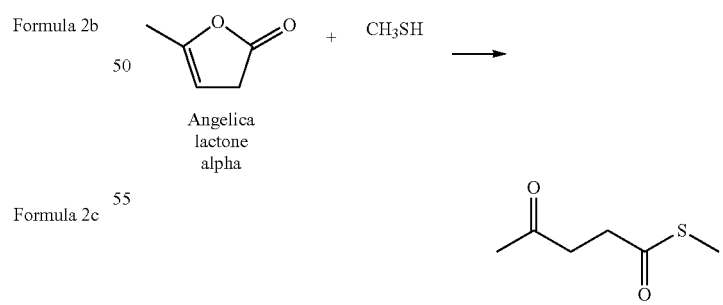

Angelica lactone alpha

Phenolic Compounds

In certain embodiments, at least one phenolic compound is present in the disclosed compositions. The phenolic compounds can be, for example, phenols, p-cresol, carvacrol, thymol, raspberry ketone, salicylates, O-acetyl substituted anisoles, and 2-alkoxy phenols. In certain embodiments, the phenolic compound is thymol. In another embodiment, the phenolic compound is raspberry ketone. In yet another embodiment, the phenolic compound is vanillin.

In certain embodiments, the phenolic compound is a salicylate. Examples of salicylate include, but are not limited to, methyl salicylate, ethyl salicylate, isobutyl salicylate, amyl salicylate, isoamyl salicylate, phenyl salicylate, benzyl salicylate, phenyl ethyl salicylate, cyclohexyl salicylate, cis-3-hexenyl salicylate, hexyl salicylate, prenyl salicylate, isopropoxy ethyl salicylate, 2-methylbutyl salicylate, and p-cresyl salicylate. In one embodiment, the phenolic compound is methyl salicylate.

In certain embodiments, the phenolic compound is an O-acetyl substituted anisole. Examples of O-acetyl substituted anisole include, but are not limited to, acetyl vanillin, acetyl eugenol, and acetyl isoeugenol. In one embodiment, the phenolic compound is eugenol.

In certain embodiments, the phenolic compound is 2-alkoxy phenol. Examples of 2-alkoxy phenol include, but are not limited to, eugenol, isoeugenol, dihydro eugenol, benzyl isoeugenol, valspice (also called "creosol"), guaiacol, vanillin, ethyl vanillin, ethyl guaiacol vanillin propylene glycol acetal, ethyl vanillin propylene glycol acetal, Hotact® VBE (vanillyl butyl ether), Hotact® VEE (vanillyl ethyl ether), Hotact®-1MM (4-(methoxymethyl)-2-(3'-methoxy-4'-hydroxyphenyl)-1,3-dioxolane), zingerone, shogaol, gingerol, vanillyl alcohol, ethyl vanillyl alcohol and vanitrope. In one embodiment, the phenolic compound is eugenol. In one embodiment, the phenolic compound is Hotact® VBE (vanillyl butyl ether). In certain embodiments, the phenolic compound is Hotact® VEE. In another embodiment, the phenolic compound is vanitrope. In yet another embodiment, the phenolic compound is vanillin.

Compositions

In accordance with the presently disclosed subject matter, the malodor compositions include at least one lactone. The amount of the lactone in the malodor eliminating composition vary depending on the nature of the malodor eliminating composition. For example, the lactone can be present in an amount of from about 0.1% to about 99.9%, from about 0.1% to about 1%, from about 1% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90%, from about 906% to about 99%, from about 0.5% to about 90%, from about 0.65% to about 80%, from about 0.8% to about 70%, from about 1% to about 60%, from about 5% to about 50%, from about 10% to about 40%, from about 5% to about 10%, from about 0.1% to about 2%, from about 0.1% to about 0.2%, from about 0.2% to about 0.5%, from about 0.5% to about 1%, from 1% to about 1.2%, from about 1.2% to about 1.5%, or from about 1.5% to about 2% weight by weight of the total malodor eliminating composition.

In certain embodiments, the lactone can be present in an amount of from about 0.1% to about 10%, about 0.25% to about 10%, about 0.5% to about 100%, about 0.75% to about 10%, from about 1.5% to about 10%, from about 2% to about 10%, about 2.5% to about 10%, about 3% to about 100%, about 3.5% to about 10%, about 4% to about 10%, about 4.5% to about 10%, about 5% to about 10%, about 5.5% to about 10%, about 6% to about 10%, about 6.5% to about 10%, about 7% to about 10%, about 7.5% to about 10%, about 8% to about 10%, about 8.5% to about 10%, or about 9% to about 10% weight by weight of the total malodor eliminating composition. In certain embodiments, the lactone can be present in an amount of from about 0.1% to about 5%, about 0.25 to about 5%, about 0.5% to about 5%, about 0.75% to about 5%, from about 1.5% to about 5%, from about 2% to about 5%, about 2.5% to about 5%, about 3% to about 5%, about 3.5% to about 5%, or about 4% to about 5%, weight by weight of the total malodor eliminating composition. In certain embodiments, the lactone can be present in an amount of from about 0.0001% to about 0.1%, about 0.00015% to about 0.05%, about 0.0002% to about 0.01%, about 0.00025% to about 0.005%, about 0.0003% to about 0.001%, or about 0.00035% to about 0.0005% weight by weight of the total malodor eliminating composition.

In certain embodiments, the lactone is present in an amount of from about 30% to about 90%, about 30% to about 85%, about 30% to about 80%, about 30% to about 75%, about 30% to about 70%, about 30% to about 65%, from about 30% to about 60%, about 30% to about 55%, from about 30% to about 50%, from about 30% to about 40%, from about 40% to about 50%, from about 50% to about 60%, or from about 60% to about 70% weight by weight of the total malodor eliminating composition. In certain embodiments, the lactone is present in an amount from about 40% to about 90%, from about 45% to about 90%, from about 50% to about 90%, from about 55% to about 90%, from about 60% to about 90%, from about 65% to about 90%, from about 70% to about 90%, from about 75% to about 90%, from about 80% to about 90%, and from about 85% to about 90% weight by weight of the total malodor eliminating composition. In certain embodiments, the lactone is present in an amount of from about 30% to about 90% weight by weight of the total malodor eliminating composition. In certain embodiments, the lactone is present in an amount of from about 40% to about 50% weight by weight of the total malodor eliminating composition. In certain embodiments, the lactone is present in an amount of from about 600% to about 70% weight by weight of the total malodor eliminating composition. In certain embodiments, the lactone is present in an amount of at least about 0.001%, at least about 0.005%, at least about 0.01%, at least about 0.05%, at least about 0.1%, at least about 0.5%, at least about 1%, at least about 2%, at least about 3%, at least about 4%, at least about 5%, at least about 10%, at least about 20%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% weight by weight of the total malodor eliminating composition. In certain embodiments, the lactone is present in no more than about 95%, no more than about 90%, no more than about 85%, no more than about 80%, no more than about 75%, no more than about 700%, no more than about 65%, no more than about 60%, no more than about 55%, no more than about 50%, no more than about 45%, no more than about 40%, no more than about 35%, or no more than about 30% weight by weight of the total malodor eliminating composition.

In one embodiment, the lactone is present in an amount of about 0.1% weight by weight of the total malodor eliminating composition. In one embodiment, the lactone is present in an amount of about 0.5% weight by weight of the total malodor eliminating composition. In one embodiment, the lactone is present in an amount of about 0.8% weight by weight of the total malodor eliminating composition. In one embodiment, the lactone is present in an amount of about 1.5% weight by weight of the total malodor eliminating composition. In one embodiment, the lactone is present in an amount of about 1.8% weight by weight of the total malodor eliminating composition. In one embodiment, the lactone is present in an amount of about 2% weight by weight of the total malodor eliminating composition. In one embodiment, the lactone is present in an amount of about 2.3% weight by weight of the total malodor eliminating composition. In one embodiment, the lactone is present in an amount of about 2.5% weight by weight of the total malodor eliminating composition. In one embodiment, the lactone is present in an amount of about 3% weight by weight of the total malodor eliminating composition. In another embodiment, the lactone is present in an amount of about 8% weight by weight of the total malodor eliminating composition. In one embodiment, the lactone is present in an amount of about 10% weight by weight of the total malodor eliminating composition. In one embodiment, the lactone is present in an amount of about 13% weight by weight of the total malodor eliminating composition. In one embodiment, the lactone is present in an amount of about 25% weight by weight of the total malodor eliminating composition. In one embodiment, the lactone is present in an amount of about 26% weight by weight of the total malodor eliminating composition. In certain embodiments, the lactone is present in an amount of from about 40% weight by weight of the total malodor eliminating composition. In another embodiment, the lactone is present in an amount of from about 42% weight by weight of the total malodor eliminating composition. In one embodiment, the lactone is present in an amount of about 43% weight by weight of the total malodor eliminating composition. In yet another embodiment, the lactone is present in an amount of from about 45% weight by weight of the total malodor eliminating composition. In one embodiment, the lactone is present in an amount of about 61% weight by weight of the total malodor eliminating composition.

The phenolic compound can be present in an amount of from about 0.1% to about 99.9%, from about 0.1% to about 1%, from about 1% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90%, from about 90% to about 99%, from about 0.5% to about 90%, from about 0.65% to about 80%, from about 0.8% to about 70%, from about 1% to about 60%, from about 5% to about 50%, from about 100% to about 40%, from about 5% to about 10%, from about 0.1% to about 2%, from about 0.1% to about 0.2%, from about 0.2% to about 0.5%, from about 0.5% to about 1%, from about 1% to about 1.2%, from about 1.2% to about 1.5%, or from about 1.5% to about 2% weight by weight of the total malodor eliminating composition. In certain embodiments, the phenolic compound is present in an amount of from about 0.00001% to about 0.1%, about 0.000015% to about 0.05%, about 0.00002% to about 0.01%, about 0.000025% to about 0.005%, about 0.00003% to about 0.001%, about 0.000035% to about 0.0005%, about 0.00004% to about 0.0001%, or about 0.000045% to about 0.00005%, weight by weight of the total malodor eliminating composition. In certain embodiments, the phenolic compound is present in an amount of at least about 0.001%, at least about 0.005%, at least about 0.01%, at least about 0.05%, at least about 0.1%, at least about 0.5%, at least about 1%, at least about 2%, at least about 3%, at least about 4%, at least about 5%, at least about 10%, at least about 20%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95% weight by weight of the total malodor eliminating composition.

In certain embodiments, the phenolic compound is present in an amount of from about 10% to about 20% weight by weight of the total malodor eliminating composition. In one embodiment, the phenolic compound is present in an amount of about 11% weight by weight of the total malodor eliminating composition. In another embodiment, the phenolic compound is present in an amount of about 18% weight by weight of the total malodor eliminating composition. In certain embodiments, the phenolic compound is present in an amount of from about 1% to about 10% weight by weight of the total malodor eliminating composition. In one embodiment, the phenolic compound is present in an amount of about 0.001% weight by weight of the total malodor eliminating composition. In one embodiment, the phenolic compound is present in an amount of about 0.04% weight by weight of the total malodor eliminating composition. In one embodiment, the phenolic compound is present in an amount of about 0.4% weight by weight of the total malodor eliminating composition. In one embodiment, the phenolic compound is present in an amount of about 0.5% weight by weight of the total malodor eliminating composition. In one embodiment, the phenolic compound is present in an amount of about 1% weight by weight of the total malodor eliminating composition. In one embodiment, the phenolic compound is present in an amount of about 1.8% weight by weight of the total malodor eliminating composition. In one embodiment, the phenolic compound is present in an amount of about 3% weight by weight of the total malodor eliminating composition. In another embodiment, the phenolic compound is present in an amount of about 4% weight by weight of the total malodor eliminating composition. In one embodiment, the phenolic compound is present in an amount of about 5% weight by weight of the total malodor eliminating composition. In another embodiment, the phenolic compound is present in an amount of about 6% weight by weight of the total malodor eliminating composition. In yet another embodiment, the phenolic compound is present in an amount of about 7% weight by weight of the total malodor eliminating composition. In one embodiment, the phenolic compound is present in an amount of about 8% weight by weight of the total malodor eliminating composition. In one embodiment, the phenolic compound is present in an amount of about 10% weight by weight of the total malodor eliminating composition.

In accordance with the presently disclosed subject matter, the ratio of the lactone and phenolic compound in the malodor eliminating composition vary depending on the nature of the malodor eliminating composition. The ratio of the lactone and phenolic compound can be about 1:1. In certain embodiments, the lactone is present in an amount less than the phenolic compound. For example, the ratio of the lactone and phenolic compound can be from about 1:2 to about 1:10. In various embodiments, the ratio of the lactone and phenolic compound is about 1:2, about 1:3, about 1:4, about 1:5, about 1:6, about 1:7, about 1:8, about 1:9, or about 1:10. In one embodiment, the ratio of the lactone and phenolic compound is about 1:2.7. In one embodiment, the ratio of the lactone and phenolic compound is about 1:2.3. In one embodiment, the ratio of the lactone and phenolic compound is about 1:2.4.

In certain embodiments, the lactone is present in an amount more than the phenolic compound. For example, the ratio of the lactone and phenolic compound can be from about 2:1 to about 100:1. In certain embodiments, the ratio of the lactone and phenolic compound is from about 10:1 to about 100:1. In various embodiments, the ratio of the lactone and phenolic compound is about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 30:1, about 40:1, about 50:1, about 60:1, about 70:1, about 80:1, about 90:1, or about 100:1. In one embodiment, the ratio of the lactone and phenolic compound is about 4:1. In another embodiment, the ratio of the lactone and phenolic compound is about 10:1. In another embodiment, the ratio of the lactone and phenolic compound is about 11:1.

In accordance with the presently disclosed subject matter, the end product comprises the presently disclosed malodor eliminating compositions and a solvent suitable for use in an end product (e.g., a solvent suitable for use in a mouthwash or fragrance). In certain embodiments, the solvent is an organic solvent. In certain embodiments, the organic solvent includes, but not limited to lower alcohols such as ethanol, 1-propanol, 2-propanol, 2,2-dimethyl-1-propanol, 2-methyl-1-propanol, 1-butanol, 2-butanol, and tert-butanol; higher alcohols such as 2-hexyldecanol, oleyl alcohol, 2-octyldodecanol, butyl alcohol, cetanol, and stearyl alcohol; polyols such as glycerin, diglycerin, polyglycerin, ethylene glycol, diethylene glycol, triethylene glycol, polyethylene glycol, propylene glycol, dipropylene glycol, isoprene glycol, 3-methyl-1,3-butanediol, 1,3-butanediol, sorbitol, and maltitol; hydrocarbons such as squalane, liquid paraffin, liquid lanolin, vaseline, and solid paraffin; esters such as isopropyl palmitate, butyl stearate, isopropyl myristate, diethyl phthalate, myristyl lactate, diisopropyl adipate, cetyl myristate, cetyl lactate, 1-isostearoyl-3-myristoylglycerol, cholesteryl isostearate, cetyl 2-ethylhexanoate, 2-ethylhexyl palmitate, 2-octyldodecyl myristate, neopentylglycol di-2-ethylhexanoate, 2-octyldodecyl oleate, glycerol triisostearate, dicaprylyl carbonate, and glyceryl di-para-methoxycinnamate mono-2-ethylhexanoate; glycol ethers such as ethylene glycol monomethyl ether, ethylene glycol monoethyl ether, ethylene glycol monopropyl ether, diethylene glycol monomethyl ether, diethylene glycol monoethyl ether, diethylene glycol monopropyl ether, propylene glycol monoethyl ether, propylene glycol monopropyl ether, dipropylene glycol monomethyl ether, ethylene glycol dimethylether, diethylenegylcol dimethylether, and dipropylene glycol mono-propyl ether, fats and fatty oils such as safflower oil, sunflower oil, rosemary oil, jojoba oil, Macadamia nut oil, olive oil, camellia oil, castor oil, orange oil, rice bran oil, triethylhexanoin, and glyceryl tri(caprylate/caprate); silicone oils including linear chain polysiloxanes such as dimethyl polysiloxane, methyl phenyl polysiloxane, and diphenyl polysiloxane, cyclic polysiloxanes such as octamethylcyclotetrasiloxane, decamethylcyclopentasiloxane, and dodecamethylcyclohexasiloxane, modified polysiloxanes such as amino-modified polysiloxanes, polyether-modified polysiloxanes, alkyl-modified polysiloxanes, and fluorine-modified polysiloxanes, and the like; triethyl citrate, triacetine (glycerin triacetate) and MCT (medium chain triglyceride); and the like.

In one embodiment, the solvent is a diol solvent or alcohol. In certain embodiments, the diol solvent or alcohol is selected from the group consisting of 3-(1-menthoxy) propane-1,2-diol (commercially available from Takasago Int'l Corp), p-menthane-3,8-diol (commercially available from Takasago Int'l. Corp.), propylene glycol, dipropylene glycol, ethyl alcohol, and combinations thereof. In one embodiment, the solvent is propylene glycol.

The solvent can be present in an amount of from about 0.1% to about 99.9%, from about 0.1% to about 1%, from about 1% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90%, from about 90% to about 99%, from about 0.5% to about 90%, from about 0.65% to about 80%, from about 0.8% to about 70%, from about 1% to about 60%, from about 5% to about 50%, from about 10% to about 40%, from about 5% to about 10%, from about 0.1% to about 2%, from about 0.1% to about 0.2%, from about 0.2% to about 0.5%, from about 0.5% to about 1%, from 1% to about 1.2%, from about 1.2% to about 1.5%, or from about 1.5% to about 2% weight by weight of the total malodor eliminating composition. The solvent can be present in an amount of from about 10% to about 90%, about 25% to about 35%, about 20% to about 60%, about 20% to about 70%, about 20% to about 80%, about 35% to about 67%, about 35% to about 40%, about 40% to about 60%, or about 60% to about 70% weight by weight of the total malodor eliminating composition. In certain embodiments, the solvent can be present in an amount of from about 0.0001% to about 0.1%, about 0.00015% to about 0.05%, about 0.0002% to about 0.01%, about 0.00025% to about 0.005%, about 0.0003% to about 0.001%, or about 0.00035% to about 0.0005% weight by weight of the total malodor eliminating composition.

In yet another embodiment, the solvent is present in an amount of about 25% weight by weight of the total malodor eliminating composition. In yet another embodiment, the solvent is present in an amount of about 35% weight by weight of the total malodor eliminating composition. In yet another embodiment, the solvent is present in an amount of about 40% weight by weight of the total malodor eliminating composition. In yet another embodiment, the solvent is present in an amount of about 67% weight by weight of the total malodor eliminating composition.

In certain embodiments, the malodor eliminating compositions can further include at least one malodor masking compound. In certain embodiments, the malodor masking compound is selected from the group consisting of, but not limited to, menthol, anisyl acetate, ethyl acetate, phenethyl alcohol, ethyl 2-methyl butyrate, ethyl butyrate, citrus oils, peppermint oil, spearmint oil, oil of wintergreen, cinnamon, ginger, and combinations thereof.

The malodor masking compound can be present in an amount of from about 0.1% to about 99.9%, from about 0.1% to about 1%, from about 1% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90%, from about 90% to about 99%, from about 0.5% to about 90%, from about 0.65% to about 80%, from about 0.8% to about 70%, from about 1% to about 60%, from about 5% to about 50%, from about 10% to about 40%, from about 5% to about 10%, from about 0.1% to about 2%, from about 0.1% to about 0.2%, from about 0.2% to about 0.5%, from about 0.5% to about 1%, from 1% to about 1.2%, from about 1.2% to about 1.5%, or from about 1.5% to about 2% weight by weight of the total malodor eliminating composition. In certain embodiments, the masking compound can be present in an amount of from about 0.0001% to about 0.1%, about 0.00015% to about 0.05%, about 0.0002% to about 0.01%, about 0.00025% to about 0.005%, about 0.0003% to about 0.001%, or about 0.00035% to about 0.0005% weight by weight of the total malodor eliminating composition. In certain embodiments, the masking agent can be present in an amount of from about 0.1% to about 90%, about 0.1% to about 0.3%, about 0.1% to about 0.47%, about 0.1% to about 1.5%, about 0.1% to about 2%, about 0.1% to about 2.5%, about 2% to about 4%, about 25 to about 7%, about 2% to about 10%, about 2% to about 12%, about 2% to about weight by weight of the total malodor eliminating composition. In yet another embodiment, the malodor masking compound is present in an amount of about 50% to about 99%, about 40% to about 99%, about 40% to about 60%, about 60% to about 80%, or about 60% to about 90% weight by weight of the total malodor eliminating composition.

In yet another embodiment, the malodor masking compound is present in an amount of about 0.1% weight by weight of the total malodor eliminating composition. In yet another embodiment, the malodor masking compound is present in an amount of about 0.3% weight by weight of the total malodor eliminating composition. In yet another embodiment, the malodor masking compound is present in an amount of about 0.4% weight by weight of the total malodor eliminating composition. In yet another embodiment, the malodor masking compound is present in an amount of about 1.5% weight by weight of the total malodor eliminating composition. In yet another embodiment, the malodor masking compound is present in an amount of about 2% to about 15%, about 2% to about 20%, about 2% to about 30%, about 2% to about 50%, about 2% to about 60%, about 2% to about 70%, about 2% to about 80%, or about 2% to about 85% weight by weight of the total malodor eliminating composition. In yet another embodiment, the malodor masking compound is present in an amount of about 2.5% weight by weight of the total malodor eliminating composition. In yet another embodiment, the malodor masking compound is present in an amount of about 3% weight by weight of the total malodor eliminating composition. In yet another embodiment, the malodor masking compound is present in an amount of about 4% weight by weight of the total malodor eliminating composition. In yet another embodiment, the malodor masking compound is present in an amount of about 7% weight by weight of the total malodor eliminating composition. In yet another embodiment, the malodor masking compound is present in an amount of about 10% weight by weight of the total malodor eliminating composition. In yet another embodiment, the malodor masking compound is present in an amount of about 12% weight by weight of the total malodor eliminating composition. In yet another embodiment, the malodor masking compound is present in an amount of about 16% weight by weight of the total malodor eliminating composition. In yet another embodiment, the malodor masking compound is present in an amount of 17% weight by weight of the total malodor eliminating composition. In yet another embodiment, the malodor masking compound is present in an amount of about 18% weight by weight of the total malodor eliminating composition. In yet another embodiment, the malodor masking compound is present in an amount of about 20% weight by weight of the total malodor eliminating composition. In yet another embodiment, the malodor masking compound is present in an amount of about 22% weight by weight of the total malodor eliminating composition. In yet another embodiment, the malodor masking compound is present in an amount of about 24% weight by weight of the total malodor eliminating composition. In yet another embodiment, the malodor masking compound is present in an amount of about 25% weight by weight of the total malodor eliminating composition. In yet another embodiment, the malodor masking compound is present in an amount of about 28% weight by weight of the total malodor eliminating composition. In yet another embodiment, the malodor masking compound is present in an amount of about 40% weight by weight of the total malodor eliminating composition. In yet another embodiment, the malodor masking compound is present in an amount of about 50% weight by weight of the total malodor eliminating composition. In yet another embodiment, the malodor masking compound is present in an amount of about 67% weight by weight of the total malodor eliminating composition. In yet another embodiment, the malodor masking compound is present in an amount of about 85% weight by weight of the total malodor eliminating composition.

In certain embodiments, the malodor eliminating compositions can further include at least one excipient. In certain embodiments, the excipient can be, but not limited to, zinc salt, stannous salt, baking soda, a polyphenol, an essential oil, and/or an anti-bacterial agent, e.g., quaternary ammonium, cethylpyridinium chloride, cyclohexidine, triclosan, and antibacterial flavor materials, dextrose, sucrose, or other saccharides, sorbitol, mannitol, isomalitol, alcohols, insoluble fillers (e.g. elastomers, resins, fats, waxes, and oils), elastomer plasticizers, emulsifiers, diluents, softeners, water insoluble flavoring agents, water soluble buffer chemicals, antioxidants, humectants, abrasives, binders, stabilizers, disintegrants, surfactants, anti-adherents, encapsulating coating, glidants, lubricants, preservatives, sorbents, whiteners, and fluoride, edible calcium powder (e.g., calcium carbonate), silicon, a water-soluble polymer, acidifier, or a carrier.

In one embodiment, the disclosed malodor eliminating compositions are combined with and excipient such as, but not limited to, zinc salt, stannous salt, baking soda, a polyphenol, an essential oil, and/or an anti-bacterial agent, e.g., quaternary ammonium, cethylpyridinium chloride, cyclohexidine, triclosan, and antibacterial flavor materials.

End Products

The malodor eliminating compositions of the presently disclosed subject matter can be used in various oral care end products including, but not limited to, toothpaste, toothpowder, tooth gels, mouthwash or mouthrinse consumer products, dental flosses, denture care products, confections (e.g., hard or soft candies), breath mints, tablets, dissolvable breath strips, gum, lozenges, and pharmaceutical or medicinal products (e.g., pharmaceutical products suitable for buccal administration).

In certain embodiments, the malodor eliminating compositions are used in foods and beverages including, but not limited to, beverages such as fruit juice beverages, sports drinks, vegetable juices, fermented lactic drinks, carbonated beverages, coffee, cocoa, teas (e.g., black, oolong green), sake, alcohol, and powdered drinks; confectionery products such as candy, chewing gum, tabletted candy, gummy candy, soda-pop candy, and chocolate; bakery products such as cookies, biscuits, and breads; deserts such as yogurt, ice cream, and jam; snacks such as potato chips and cracker, stew, curry, soup, dressing, dip, noodle soup, bouillon stock, miso, instant bouillon, sauce, bouillon, miso soup, pickles, rice-ball topping, topping for tea and rice, semi-cooked or cooked foods such as wheat, buckwheat, and noodles, or the chilled and frozen foods thereof; instant foods such as instant noodle; seasoning such as mixed powdery seasonings; salad dressings and condiments such as mayonnaise, mustard, and onion-based foods; garlic-based foods; and eggs, and egg based products. The malodor eliminating compositions of the presently disclosed subject matter can be used in various consumer products including, but not limited to, milk, condensed milk, evaporated milk, skimmed milk, butter, cream, whipped cream, dairy flavorings, yogurt, cheese, cream cheese, or sour cream.

In certain embodiments, the malodor eliminating compositions are used in personal care products including, but not limited to, shampoo, rinse, rinse-in-shampoo, hair conditioner, hair treatment, hair pack, hairspray, dry shampoos, bath soap, perfume soap, clear soap, synthetic soap; body soap, body shampoo, hand soap, bath salt, bath tablet, foam bath (e.g., bubble bath, bath oil such as bath perfume and bath capsule), milk bath, bath jelly, and bath cube.

In certain embodiments, the malodor eliminating compositions are used in cleaning products including, but not limited to, detergent for clothes, liquid laundry detergent, laundry soap, compact detergent, all-purpose detergents, softener, household cleaners, house wash, toilet cleaner, bath cleaner, glass cleaner, fungicide, and cleaner for drain pipe kitchen soap, kitchen synthetic soap, and dish wash detergent, beaching agent, oxidant bleach (e.g. chlorine bleach and oxygen bleach), reductive bleach (e.g., sulfur containing bleach), optical bleach, spray aerosol, powder spray, deodorant-aromatics (e.g., solid, gel and liquid deodorizer), aromatics, car fresheners, room fresheners, candles, and carpet deodorizers.

In certain embodiments, the malodor eliminating compositions are used in animal care products including, but not limited to, shampoos, bath powders, dry shampoos, cleaning cloths, deodorizing sprays, pet bedding deodorant, pet tooth pastes, chew toys, pet food, pet treats, cat litter, cat litter liners, and cat litter box deodorants.

As understood by the skilled flavorist or fragrance specialist, the use level (or total amount) of the malodor eliminating composition in a given end product can vary depending on the end product to which it is added, the taste or scent profile desired by the skilled flavorist or fragrance specialist, and processing. It is also likely that the different combinations of the components or ingredients of the malodor eliminating compositions could result in higher or lower use levels depending on the application and the formulation of an end product (e.g., whether it is a toothpaste or in the form of a gel).

In certain embodiments, the malodor eliminating compositions of the presently disclosed subject matter are sufficiently hydrophilic such that the components or ingredients of the compositions, including lactones and possibly phenolic compounds, can react with malodor causing constituents, such as a thiol and an amine in a polar environment (such as, but not limited to water, alcohol, or diol solvent (e.g., propylene glycol)). In certain embodiments, the malodor eliminating compositions are particularly suitable for malodor elimination in aqueous environment, such as the oral cavity.

Thus, in certain embodiments, the malodor eliminating compositions of the presently disclosed subject matter are combined with a suitable solvent and used in (e.g., in creating) a consumer product, for example, an oral personal end product. The malodor eliminating compositions impart pleasant effects to the oral care end products that consumers generally find pleasing. A suitable solvent is a solvent that, when combined with other components of an end product, will not render the end product unfit for its intended use. For example and without limitation, a solvent suitable for use in a mouthwash or mouthrinse must be one that does not compromise the ability of the end product to be orally consumed as indicated (e.g., gargled, rinsed and/or swallowed).

In one embodiment, the end product is a mouthwash or mouthrinse consumer product. The use level of a malodor eliminating composition is from about 0.001% to about 3%, from about 0.01% to about 1.5%, from about 0.05% to about 1%, or from about 0.1% to about 0.5% weight by weight of the total mouthwash or mouthrinse consumer product.

A mouthwash or mouthrinse consumer product can be prepared by any suitable processes known to one skilled in the art. For example, a mouthwash or mouthrinse consumer product can be prepared by dissolving a malodor eliminating composition (present in liquid or powder form) in a suitable solvent that further includes, for example, a flavor such as menthol and a surfactant; and then mixing the resulting solution with, for example, an aqueous erythritol solution. In certain embodiments, the flavor is present from about 0.05% to about 0.5%, from about 0.075% to about 0.45%, from about 0.1% to about 0.4%, from about 0.25% to about 0.35%, from about 0.1% to about 0.4%, or from about 0.2% to about 0.5% weight by weight of the total mouthwash or mouthrinse consumer product. In certain embodiments, the favor is present from at least about 0.05%, from at least about 0.06%, from at least about 0.07%, from at least about 0.08%, from at least about 0.09%, from at least about 0.1%, from at least about 0.2%, from at least about 0.3%, from at least about 0.4%, or from at least 0.5% weight by weight of the total mouthwash or mouthrinse consumer product. In certain embodiments, the surfactant is present at about 2 to about 5, from about 3 to about 5, from about 4 to about 5, from about 3 to about 4 times the amount of the flavor.

In one embodiment, the end product is a toothpaste consumer product. The use level of a malodor eliminating composition is from about 0.1% to about 3.0%, from about 0.5% to about 2.0%, from about 0.65% to about 1.65%, or from about 0.8% to about 1.3% weight by weight of the total toothpaste consumer product.

In one embodiment, the end product is a dental floss. The use level of a malodor eliminating composition is from about 0.2% to about 3.5%, from about 0.4% to about 3.0%, from about 0.6% to about 2.5%, or from about 0.8% to about 2% weight by weight of the total coating of a dental floss consumer product.

In one embodiment, the end product is a denture adhesive product. The use level of a malodor eliminating composition is from about 0.05% to about 10%, from about 0.1% to about 9%, from about 0.15% to about 8%, from about 1% to about 7%, from about 1.5% to about 6%, from about 2% to about 5%, or from about 2.5% to about 4% weight by weight of the total denture adhesive product.

In one embodiment, the end product is a denture cleaner (e.g., paste, gel, powder, etc. . . . ) product. The use level of a malodor eliminating composition is from about 0.05% to about 10%, from about 0.1% to about 9%, from about 0.15% to about 8%, from about 1% to about 7%, from about 1.5% to about 6%, from about 2% to about 5%, or from about 2.5% to about 4% weight by weight of the total denture cleaner product.

In one embodiment, the end product is a chewing gum. The use level of a malodor eliminating composition is from about 0.1% to about 6.0%, from about 0.15% to about 5.5%, from about 0.2% to about 5.0%, from about 0.25% to about 4.5%, from about 0.3% to about 4.0%, from about 0.35% to about 3.5%, from about 0.4% to about 3.0%, from about 0.45% to about 2.5%, from about 0.5% to about 2.0%, from about 0.55% to about 1.5%, or from about 0.6% to about 1.0% weight by weight of the total chewing gum product.

In one embodiment, the end product is a tablet. The use level of a malodor eliminating composition is from about 0.05% to about 10%, from about 0.1% to about 9%, from about 0.15% to about 8%, from about 1% to about 7%, from about 1.5% to about 6%, from about 2% to about 5%, or from about 2.5% to about 4% weight by weight of the total tablet product.

In one embodiment, the end product is a pastille. The use level of a malodor eliminating composition is from about 0.1% to about 6.0%, from about 0.15% to about 5.5%, from about 0.2% to about 5.0%, from about 0.25% to about 4.5%, from about 0.3% to about 4.0%, from about 0.35% to about 3.5%, from about 0.4% to about 3.0%, from about 0.45% to about 2.5%, from about 0.5% to about 2.0%, from about 0.55% to about 1.5%, or from about 0.6% to about 1.0% weight by weight of the total pastille product.

In one embodiment, the end product is a hard candy. The use level of a malodor eliminating composition is from about 0.1% to about 6.0%, from about 0.15% to about 5.5%, from about 0.2% to about 5.0%, from about 0.25% to about 4.5%, from about 0.3% to about 4.0%, from about 0.35% to about 3.5%, from about 0.4% to about 3.0%0, from about 0.45% to about 2.5%, from about 0.5% to about 2.0%, from about 0.55% to about 1.5%, or from about 0.6% to about 1.0% weight by weight of the total hard candy product.

The malodor eliminating compositions, and end products containing them can further include additional flavor ingredients and excipients that are well-known in the art. Examples of known flavor ingredients can be found in the Flavor and Extracts Manufacturers Association of the United States (FEMA) publications, particularly those compounds generally recognized as safe (FEMA-GRAS) materials. Malodor eliminating compositions of the presently disclosed subject matter may further include one or more components described in Allured's Flavor and Fragrance Materials (2004), published by Allured Publishing Inc.

EXAMPLES

The following examples are merely illustrative of the presently disclosed subject matter and they should not be considered as limiting the scope of the presently disclosed subject matter in any way.

Screening Examples

Summary

Examples 1-6 illustrate a series of screening assays to identify and target compounds useful for malodor eliminating compositions.

Methyl mercaptan suppression analysis was used to evaluate malodor elimination effects of the compounds. Methyl mercaptan is known to be a major oral malodor material. For example, methyl mercaptan is found in the oral cavity of halitosis patients and also found in malodor producing food products (e.g., garlic). A multipurpose sampler (MPS 2, Gerstel Inc, Baltimore Md.)—Gas Chromatography (6890N, Agilent Technologies Inc, Wilmington Del.) with the Pulsed Flame Photometric Detector (PFPD, model 5380, OI Analytical, College Station, Tx) was used for the methyl mercaptan analysis. 0.5% (w/v) sodium thiomethoxide, which is a sodium salt of methyl mercaptan (purchased from Aldrich chemical company, Inc. Allentown, Pa.) in deionized water was used as the methyl mercaptan stock solution, which was freshly prepared for every test day.

Methods and Materials Examples 1-4

200 ppm or 100 ppm lactone (36 µl of 1% (200 ppm) or 0.5% (100 ppm) (w/v) of the test malodor eliminating compounds in 200 proof ethanol), 144 µl of 200 proof ethanol, and 1620 µl of deionized water were added into a 2 ml GC vial. The prepared vial was placed on a sample tray of the multipurpose sampler-GC-PFPD. 3.6 µl of methyl mercaptan stock solution was added in the GC vial using the multipurpose sampler, and the GC vial was left to sit at room temperature for 2 hours. 0.4 µl of the test solution was injected into the GC inlet (an Agilent tapered focus liner with glass wool was installed, split mode, 10:1 split ratio) using the multipurpose sampler. The carrier gas flow rate was 1.5 ml/min (in constant flow mode) and the Agilent DB-1MS UI column (L60 m×ID 0.250 mm×thickness 0.25 µm) was used for the analysis. The initial temperature of the GC oven was 40° C. and was increased to 180° C. after 5 minutes at a speed of 20° C./min, which was subsequently increased to 280° C. at a speed of 40° C./min. The GC oven was held at 280° C. for 5 minutes. Ethanol alone was used as a blank control. The final concentration of test malodor eliminating compounds were 200 ppm or 100 ppm, and final methyl mercaptan sodium salt concentration was about 10 ppm.

Malodor (methyl mercaptan) suppression was calculated as follows: Malodor (methyl mercaptan) suppression was calculated as follows: Malodor (methyl mercaptan) Suppression (%)=(GC area of blank control sample−GC area of test sample)/GC area of blank control sample×100.

Methods and Materials for Examples 5-9

For the screening test, 100 ppm lactone (20 µl of 0.5% of lactone in 200 proof ethanol (w/v)), 300 ppm lactone (30 µl of 1% of lactone in 200 proof ethanol (w/v)), 200 ppm phenolic compound (20 µl of 1% of phenolic compound in 200 proof ethanol (w/v)) and 300 ppm phenolic compound (30 µl of 1% of phenolic compound in 200 proof ethanol (w/v)) were tested. In addition, various combinations of a lactone and a phenolic compound were tested. The lactones and phenolic compounds were pipetted into 2 ml GC vials, and 200 proof ethanol was added up to 1000 µl. The prepared vial was placed on a sample tray of the multipurpose sampler-GC-PFPD. 2 µl methyl mercaptan stock solution was added in the GC vial utilizing the multipurpose sampler, and the vial was left to sit at room temperature for 2 hours. 0.4 µl of the test solution was injected into the GC inlet (an Agilent tapered focus liner with glass wool was installed, split mode, 10:1 split ratio) using the multipurpose sampler. The carrier gas flow rate was 1.5 ml/min (in constant flow mode) and the Agilent DB-1 MS UI column (L60 m×ID 0.250 mm×thickness 0.25 µm) was used for the analysis. The temperature of the GC oven started at 40° C. and after 5 minutes, the temperature was increased to 180° C. at a speed of 20° C./min, and subsequently to 280° C. at a speed of 40° C./min, which was held for 5 minutes.

200 proof ethanol alone was used as a blank control. The final concentration of the methyl mercaptan sodium salt was 10 ppm.

Malodor (methyl mercaptan) suppression was calculated as follows: Malodor (methyl mercaptan) Suppression (%)=

(GC area of blank control sample−GC area of test sample)/GC area of blank control sample×100.

Results of Examples 1-4

Example 1

In Example 1, the malodor suppression or elimination effect provided by 200 ppm *angelica* lactone alpha was evaluated. The results are presented in Table 1.

TABLE 1

| Test Sample | Methyl Mercaptan Suppression (%) | | |
|---|---|---|---|
| 200 ppm angelica lactone alpha | 94 | 93 | 86 |

Example 2

In Example 2, the malodor suppression or elimination effect provided by 200 ppm mint lactone was evaluated. The results are presented in Table 2.

TABLE 2

| Test Sample | Methyl Mercaptan Suppression (%) | | |
|---|---|---|---|
| 200 ppm mint lactone | 87 | 100 | 100 |

Example 3

In Example 3, the malodor suppression or elimination effect provided by 100 ppm 2(5H) furanone was evaluated. The results are presented in Table 3.

TABLE 3

| Test Sample | Methyl Mercaptan Suppression (%) | | |
|---|---|---|---|
| 100 ppm 2(5H) furanone | 97 | 95 | 100 |

Example 4

In Example 4, a series of tests were conducted to evaluate the malodor suppression or elimination effect provided by 100 ppm *angelica* lactone alpha and 100 ppm *angelica* lactone beta. The results are presented in Table 4.

TABLE 4

| Test Sample | Methyl Mercaptan Suppression (%) | | |
|---|---|---|---|
| 100 ppm angelica lactone alpha | 47 | 31 | 69 |
| 100 ppm angelica lactone beta | 10 | 26 | 41 |

Discussion for Examples 1-4

As shown in Tables 1-4, lactones (e.g., *angelica* lactone alpha, *angelica* lactone beta, mint lactone, and 2(5H) furanone) suppressed the amount of methyl mercaptan.

Results of Examples 5-8

Example 5

In Example 5, a series of tests were conducted to evaluate the malodor suppression or elimination effect provided by a lactone alone (e.g., 100 ppm *angelica* lactone alpha), by a phenolic compound alone (e.g., 200 ppm eugenol, 200 ppm Hotact®VBE, 200 ppm methyl salicylate), and by a combination of a lactone and a phenolic compound (e.g., a combination of 100 ppm *angelica* lactone alpha and 200 ppm methyl salicylate). The results are presented in Table 5.

TABLE 5

| | Methyl Mercaptan Suppression (%) Testing Set | | | | | | | | | | |
|---|---|---|---|---|---|---|---|---|---|---|---|
| Test Sample | Set 1 | Set 2 | Set 3 | Set 4 | Set 5 | Set 6 | Set 7 | Set 8 | Set 9 | Set 10 | Set 11 |
| 100 ppm angelica lactone alpha | n/a | n/a | n/a | n/a | n/a | n/a | n/a | n/a | n/a | 0 | n/a |
| 200 ppm eugenol | n/a | 11 | 12 | 9 | 12 | 8 | n/a | 13 | n/a | n/a | n/a | n/a |
| 200 ppm Hotact ®VBE | 13 | 7 | n/a | 8 | 10 | n/a | n/a | n/a | n/a | n/a | n/a | n/a |
| 200 ppm methyl salicylate | 2 | n/a | 3 | 3 | 4 | 1 | 4 | 8 | 6 | −2* | 8 |
| Combination of 100 ppm angelica lactone alpha and 200 ppm methyl salicylate | n/a | n/a | n/a | n/a | n/a | n/a | n/a | n/a | n/a | 72 | n/a |

*A negative methyl mercaptan suppression value was attributed to be a result of oxidization of methyl mercaptan to dimethyl disulfide at room temperature and in the presence of ambient air.

Example 6

In Example 6, a series of tests were conducted to evaluate the malodor suppression or elimination effect provided by a lactone alone (e.g., 100 ppm *angelica* lactone alpha), by a phenolic compound alone (e.g., 200 ppm eugenol, 200 ppm Hotact®VBE, 200 ppm methyl salicylate), and by a combination of a lactone and a phenolic compound (e.g., a combination of 100 ppm *angelica* lactone alpha and 200 ppm eugenol, a combination of 100 ppm *angelica* lactone alpha and 200 ppm Hotact®VBE, and a combination of 100 ppm *angelica* lactone alpha and 200 ppm methyl salicylate). The results are presented in Table 6.

TABLE 6

Methyl Mercaptan Suppression (%) Testing Set

| Test Sample | Set 1 | Set 2 | Set 3 | Set 4 | Set 5 | Set 6 |
|---|---|---|---|---|---|---|
| 100 ppm angelica lactone alpha | n/a | n/a | 3 | 18 | 15 | 11 | -7* | n/a |
| 200 ppm eugenol | 21 | 12 | n/a | 15 | n/a | n/a |
| A combination of 100 ppm angelica lactone alpha and 200 ppm eugenol | n/a | n/a | 80 | 79 | n/a | n/a |
| 200 ppm Hotact ®VBE | 8 | 12 | n/a | 17 | n/a | n/a |
| A combination of 100 ppm angelica lactone alpha and 200 ppm Hotact ®VBE | n/a | n/a | 84 | 78 | n/a | n/a |
| 200 ppm methyl salicylate | 15 | 1 | n/a | 5 | n/a | 2 |
| Combination of 100 ppm angelica lactone alpha and 200 ppm methyl salicylate | n/a | n/a | 83 | 78 | n/a | n/a |

*A negative methyl mercaptan suppression value was attributed to be a result of oxidization of methyl mercaptan to dimethyl disulfide at room temperature and in the presence of ambient air.

Example 7

In Example 7, a series of tests were conducted to evaluate the malodor suppression or elimination effect provided by a lactone alone (e.g., 100 ppm 2(5H)furanone), by a phenolic compound alone (e.g., 200 ppm eugenol), and by a combination of a lactone and a phenolic compound (e.g., a combination of 100 ppm 2(5H)furanone and 200 ppm eugenol). The results are presented in Table 7.

TABLE 7

Methyl Mercaptan Suppression (%)

| Test Sample | Set 1 | | | Set 2 | | | Set 3 | | |
|---|---|---|---|---|---|---|---|---|---|
| 100 ppm 2(5H)furanone | -5* | -5* | -4* | 11 | 4 | 2 | -9* | -12* | -4* |
| 200 ppm eugenol | 5 | 7 | 4 | 11 | 12 | 8 | 7 | 14 | 9 |
| A combination of 100 ppm 2(5H)furanone and 200 ppm eugenol | 66 | 66 | 65 | 81 | 78 | 76 | 76 | 80 | 73 |

*A negative methyl mercaptan suppression value was attributed to be a result of oxidization of methyl mercaptan to dimethyl disulfide at room temperature and in the presence of ambient air.

Example 8

In Example 8, a single test was conducted to evaluate the malodor suppression or elimination effect provided by a lactone alone (e.g., 300 ppm *angelica* lactone alpha), by a phenolic compound alone (e.g., 300 ppm eugenol, 300 ppm Hotact®VBE, and 300 ppm methyl salicylate), and by a combination of a lactone and a phenolic compound (e.g., a combination of 100 ppm *angelica* lactone alpha and 200 ppm eugenol, a combination of 100 ppm *angelica* lactone alpha and 200 ppm Hotact®VBE, and a combination of 100 ppm *angelica* lactone alpha and 200 ppm methyl salicylate). The results are presented in Table 8.

TABLE 8

| Test Sample | Methyl Mercaptan Suppression (%) | | |
|---|---|---|---|
| 300 ppm angelica lactone alpha | 32 | 22 | 30 |
| 300 ppm eugenol | 8 | 14 | 11 |
| A combination of 100 ppm angelica lactone alpha and 200 ppm eugenol | 76 | 76 | n/a |
| 300 ppm Hotact ®VBE | 13 | 13 | 10 |
| A combination of 100 ppm angelica lactone alpha and 200 ppm Hotact ®VBE | 80 | 80 | n/a |
| 300 ppm methyl salicylate | 9 | 10 | 8 |
| Combination of 100 ppm angelica lactone alpha and 200 ppm methyl salicylate | 76 | 78 | n/a |

Example 9

In Example 9, a series of tests were conducted to evaluate the malodor suppression or elimination effect provided by 200 ppm furaneol or 200 ppm ascorbic acid alone or in combination with 200 ppm methyl salicylate. The results are presented in Table 9.

TABLE 9

| Test Sample | Methyl Mercaptan Suppression (%) | |
|---|---|---|
| 200 ppm furaneol | 2 | n/a |
| 200 ppm methyl salicylate | 2 | -2* |
| A combination of 200 ppm furaneol and 200 ppm methyl salicylate | 3 | 2 |
| 200 ppm ascorbic acid | 11 | n/a |
| A combination of 200 ppm ascorbic acid and 200 ppm methyl salicylate | 11 | n/a |

*A negative methyl mercaptan suppression value was attributed to be a result of oxidization of methyl mercaptan to dimethyl disulfide at room temperature and in the presence of ambient air.

Discussion for Examples 5-9

Examples 1-4 were run using aqueous conditions, while Examples 5-9 were conducted using non-aqueous (ethanol) conditions. It should be noted that the activity of lactones in ethanol is lower than the activity achieved in aqueous conditions. As shown in Tables 5-8, various combinations of a single lactone (e.g., *angelica* lactone alpha and 2(5H)furanone) combined with a single phenolic compound (e.g., eugenol, Hotact®VBE, and methyl salicylate) showed remarkably higher malodor suppression or elimination effect than an additive effect of a lactone plus a phenolic compound. Example 9 demonstrates that the synergistic effects of Examples 5-8 are particular to the lactone and phenolic combinations. In particular, Example 9 demonstrates that compounds similar in structure to the lactones of Examples 5-8 (e.g., furaneol and ascorbic acid) do not exhibit a synergistic malodor elimination effect when combined with phenolic compounds.

Thus, the results support that a combination of one lactone and one phenolic compound exhibits an unexpected synergistic suppression or elimination effect.

Formulations Examples

The following Examples 10-25 present various flavor formulations that encompass the presently disclosed malodor eliminating compositions.

Example 10

A Raspberry Flavored Candy Formulation A in accordance with the presently disclosed subject matter, e.g., including at least one lactone and at least one phenolic compound, is shown in Table 10.

TABLE 10

|  | Formulation A ingredients | Quantity (kg) | Weight % |
|---|---|---|---|
| Lactone | Undecalactone, gamma | 150.0000 | 2.5000 |
| Phenolic compounds | Ethyl vanillin | 300.0000 | 5.0000 |
|  | Vanillin | 60.0000 | 1.0000 |
|  | Hydroxyphenyl-p(4)-2-butanone (Raspberry ketone) | 50.0000 | 0.8333 |
| Flavor material | Aldehyde C-16 pure | 200.0000 | 3.3333 |
|  | Acetyl methyl carbinol | 30.0000 | 0.5000 |
|  | Menthol-L pellets/flakes synthetic USP (Mint ICC) | 1230.0000 | 20.5000 |
|  | Isoamyl acetate | 280.0000 | 4.6667 |
|  | Isoamyl butyrate | 650.0000 | 10.8333 |
|  | Isoamyl propionate | 350.0000 | 5.8333 |
|  | Anisyl acetate | 150.0000 | 2.5000 |
|  | Benzyl acetate | 110.0000 | 1.8333 |
|  | Benzyl butyrate | 250.0000 | 4.1667 |
|  | Benzyl propionate | 400.0000 | 6.6667 |
|  | Butyl acetate | 200.0000 | 3.3333 |
|  | Ethyl butyrate | 1000.0000 | 16.6667 |
|  | Ethyl caproate | 100.0000 | 1.6667 |
|  | Ethyl caprylate | 100.0000 | 1.6667 |
|  | Ethyl heptanoate | 20.0000 | 0.3333 |
|  | Ethyl propionate | 120.0000 | 2.0000 |
|  | Styralyl acetate | 250.0000 | 4.1667 |
|  | Totals | 6,000.00 | 100.00 |

Example 11

A Raspberry Flavored Mouthrinse Formulation B in accordance with the presently disclosed subject matter, e.g., including at least one lactone and at least one phenolic compound, is shown in Table 11.

TABLE 11

|  | Formulation B ingredients | Quantity (kg) | Weight % |
|---|---|---|---|
| Lactone | Undecalactone gamma | 150.0000 | 1.5000 |
|  | Angelica lactone alpha 98% | 4000.0000 | 40.0000 |
|  | Mint lactone | 10.0000 | 0.1000 |
| Phenolic compounds | Ethyl vanillin | 300.0000 | 3.0000 |
|  | Vanillin | 60.0000 | 0.6000 |
|  | Hydroxyphenyl-P(4)-2-Butanone (Raspberry ketone) | 50.0000 | 0.5000 |
| Flavor material | Aldehyde C-16 pure | 200.0000 | 2.0000 |
|  | Acetyl methyl carbinol | 30.0000 | 0.3000 |
|  | Menthol-L pellets/flakes Synthetic USP (Mint ICC) | 1220.0000 | 12.2000 |
|  | Isoamyl acetate | 280.0000 | 2.8000 |
|  | Isoamyl butyrate | 650.0000 | 6.5000 |
|  | Isoamyl propionate | 350.0000 | 3.5000 |
|  | Anisyl acetate | 150.0000 | 1.5000 |
|  | Benzyl acetate | 110.0000 | 1.1000 |
|  | Benzyl butyrate | 250.0000 | 2.5000 |
|  | Benzyl propionate | 400.0000 | 4.0000 |
|  | Butyl acetate | 200.0000 | 2.0000 |
|  | Ethyl butyrate | 1000.0000 | 10.0000 |
|  | Ethyl caproate | 100.0000 | 1.0000 |
|  | Ethyl caprylate | 100.0000 | 1.0000 |
|  | Ethyl heptanoate | 20.0000 | 0.2000 |
|  | Ethyl propionate | 120.0000 | 1.2000 |
|  | Styralyl acetate | 250.0000 | 2.5000 |
|  | Totals | 10,000.00 | 100.00 |

Example 12

A Vanilla Flavored Toothpaste Formulation C in accordance with the presently disclosed subject matter, e.g., including at least one lactone and at least one phenolic compound, is shown in Table 12.

TABLE 12

|  | Formulation C ingredients | Quantity (kg) | Weight % |
|---|---|---|---|
| Lactone | Decalactone delta | 160.0000 | 2.6667 |
|  | Cyclohexyl lactone | 200.0000 | 3.3333 |
|  | Octalactone gamma | 50.0000 | 0.8333 |
|  | Natactone dextro 10% Triacetin | 50.0000 | 0.8333 |
| Phenolic compounds | Ethyl vanillin | 600.0000 | 10.0000 |
|  | Vanillin | 480.0000 | 8.0000 |
| Flavor material | Benzaldehyde | 40.0000 | 0.6667 |
|  | Heliotropine | 80.0000 | 1.3333 |
|  | Butyl butyryl lactate | 80.0000 | 1.3333 |
|  | Acetyl methyl carbinol | 20.0000 | 0.3333 |
|  | 2-Acetyl pyrazine@ 1% PG | 200.0000 | 3.3333 |
| Solvent | Propylene glycol | 4040.0000 | 67.3334 |
|  | Totals | 6,000.00 | 100.00 |

Example 13

A Vanilla Flavored Mouthrinse Formulation D in accordance with the presently disclosed subject matter, e.g., including at least one lactone and at least one phenolic compound, is shown in Table 13.

TABLE 13

|  | Formulation D ingredients | Quantity (kg) | Weight % |
|---|---|---|---|
| Lactone | Decalactone delta | 160.0000 | 1.6000 |
|  | Cyclohexyl lactone | 200.0000 | 2.0000 |
|  | Angelica lactone Alpha 98% | 4000.0000 | 40.0000 |
|  | Natactone dextro 10% Triacetin | 50.0000 | 0.5000 |
|  | Octalactone gamma | 50.0000 | 0.5000 |
| Phenolic compounds | Ethyl vanillin | 600.0000 | 6.0000 |
|  | Vanillin | 480.0000 | 4.8000 |
| Flavor material | Benzaldehyde | 40.0000 | 0.4000 |
|  | Heliotropine | 80.0000 | 0.8000 |
|  | Butyl butyryl lactate | 80.0000 | 0.8000 |
|  | Acetyl methyl carbinol | 20.0000 | 0.2000 |
|  | 2-Acetyl pyrazine@ 1% PG | 200.0000 | 2.0000 |
| Solvent | Propylene glycol | 4040.0000 | 40.4000 |
|  | Totals | 10,000.00 | 100.00 |

Example 14

A Condensed Milk Lactonic Formulation E in accordance with the presently disclosed subject matter, e.g., including at least one lactone, is shown in Table 14.

TABLE 14

| Formulation E ingredients | | Quantity (kg) | Weight % |
|---|---|---|---|
| Lactone | Angelica lactone natural | 260.0000 | 26.0000 |
|  | Dodecalactone delta natural | 250.0000 | 25.0000 |
|  | Decalactone delta natural | 100.0000 | 10.0000 |
| Flavor material | Caproic acid natural | 100.0000 | 10.0000 |
|  | Sulfurol Natural | 40.0000 | 4.0000 |
| Solvent | Propylene glycol | 250.0000 | 25.0000 |
|  | Totals | 10,000.00 | 100.00 |

Example 15

A Tropical Formulation F in accordance with the presently disclosed subject matter, e.g., including at least one lactone, is shown in Table 15.

TABLE 15

| Formulation F ingredients | | Quantity (kg) | Weight % |
|---|---|---|---|
| Lactone | Angelica lactone alpha 98% | 4000.0000 | 40.0000 |
|  | Undecalactone gamma | 300.0000 | 3.0000 |
| Flavor material | Allyl cyclohexyl propionate | 100.0000 | 1.0000 |
|  | Piperonyl acetone | 220.0000 | 2.2000 |
|  | Benzyl acetate | 280.0000 | 2.8000 |
|  | Dimethyl benzyl carbinyl acetate | 80.0000 | 0.8000 |
|  | Butyl butyrate | 160.0000 | 1.6000 |
|  | Butyl butyryl lactate | 80.0000 | 0.8000 |
|  | Ethyl aceto acetate | 200.0000 | 2.0000 |
|  | Ethyl lactate | 120.0000 | 1.2000 |
|  | Geranyl acetate | 20.0000 | 0.2000 |
|  | Hexyl acetate | 300.0000 | 3.0000 |
|  | Hexyl butyrate | 800.0000 | 8.0000 |
|  | Ethyl 2-methylbutyrate | 200.0000 | 2.0000 |
|  | Octen-cis-5 1-OL | 120.0000 | 1.2000 |
|  | Phenyl ethyl alcohol | 60.0000 | 0.6000 |
|  | Mentha-para-8 thiol-3-one, 10% triglycerides | 40.0000 | 0.4000 |
|  | Orange oil 10x Natural | 2800.0000 | 28.0000 |
|  | Methyl 3-methyl thiopropionate | 20.0000 | 0.2000 |
|  | Methyl2-4Propyl1,3Oxathiane, 1% triacetin | 100.0000 | 1.0000 |
|  | Total | 10,000.00 | 100.00 |

Example 16

A Spearmint Flavored Breath Mint Formulation G in accordance with the presently disclosed subject matter, e.g., including at least one lactone and at least one phenolic compound, as shown in the Table 16, was made.

TABLE 16

Formulation G ingredients
Micron spearmint was spray dry, while the rest of the ingredients were liquid
Use level 0.9% in product

| | | Weight % |
|---|---|---|
| Lactone | Angelica lactone alpha | 1.7778 |
| Flavor material | Micron spearmint | 77.7778 |
|  | Spearmint oil FWN TYPE GCC | 0.4444 |
|  | Spearmint oil MWS TYPE GCC | 0.3333 |
|  | Carvone | 13.3333 |
|  | Piperitone Nat | 3.1111 |

TABLE 16-continued

| | | |
|---|---|---|
|  | Damascone beta | 0.0222 |
|  | Artificial spearmint leaf key | 0.0889 |
|  | Artificial peppermint extender* | 3.1111 |
|  | Totals | 100.0000 |

*Artificial peppermint extender contains material below(% in whole flavor)

| | | |
|---|---|---|
| Lactone | Mint lactone | 0.0002 |
|  | Cyclohexyl lactone | 0.0002 |
| Phenolic compounds | Thymol | 0.0001 |
|  | Vanillin | 0.00001 |
|  | Acetyl eugenol | 0.0031 |
|  | Additional Ingredients | 3.1074 |

Example 17

A Peppermint Flavored Breath Mint Formulation H in accordance with the presently disclosed subject matter, e.g., including at least one lactone and at least one phenolic compound, as shown in the Table 17, was made.

TABLE 17

| Formulation H ingredients | | Weight % |
|---|---|---|
| Lactone | Angelica lactone alpha 98% | 1.7778 |
| Water | Water City NAT | 29.1667 |
| Sweetener | Maltodextrin M100 (NON-GMIP SYN) | 31.1111 |
| Excipient | Starch Modified Capsule (NON-GMIP SYN) | 7.7778 |
| Flavor material | Intensates ® N&A peppermint extra flavor | 9.7222 |
|  | Mint sweet section* | 0.4444 |
|  | Mint filter | 0.1333 |
|  | Butyl iso valerate 10% menthone SYN | 0.0889 |
|  | Isobutyric ald 10% menthone SYN | 0.0889 |
|  | Caryophyllene FCC NAT | 0.4444 |
|  | Eucalyptol NAT FCC (NF) GCC | 1.7778 |
|  | Limonene-L 80 | 1.0667 |
|  | Squint NAT | 0.1333 |
|  | Pinene alpha NAT | 0.1333 |
|  | Pinene beta | 0.1333 |
|  | Piperitone NAT | 4.4444 |
|  | Terpinene gamma | 0.0889 |
|  | Isovaleric ald 10% menthone SYN | 0.1333 |
|  | Undecatriene 1% menthone SYN | 0.1111 |
|  | Art peppermint top note main | 1.7778 |
|  | Menthol SYN USP GCC | 2.2222 |
|  | Menthyl-L acetate | 0.4444 |
|  | Damascone beta | 0.0222 |
|  | Hexenyl trans-2 acetate | 0.0889 |
|  | Carvone-L SYN GCC | 6.6667 |
|  | Totals | 100.0000 |

*Mint sweet section contains material below(% in whole flavor)
Lactone    Mint lactone         0.0033
           Hexalactone gamma    0.0343
Phenolic compound    Vanillin   0.0004
           Additional ingredients    0.4064

Shaded ingredients were spray dry. The remaining were liquid.
Use level 0.9% in product

Example 18

A Cool Mint Flavored Breath Mint Formulation 1 in accordance with the presently disclosed subject matter, e.g., including at least one lactone and at least one phenolic compound, as shown in the Table 18, was made.

TABLE 18

| Formulation I ingredients Use level 0.7% in product | | Weight % |
|---|---|---|
| Flavor material | Angelica lactone alpha 98% | 2.2857 |
| | Ethyl Vanillin | 1.7500 |
| | Vanillin | 0.3571 |
| | Vanitrope | 0.0357 |
| | Eucalyptol NAT FCC (NF) GCC | 2.1429 |
| | *Mentha arvensis* terpeneless | 17.8571 |
| | Peppermint oil willamette type GCC | 7.1429 |
| | Peppermint oil, Indian | 17.8571 |
| | Menthol SYN USP GCC | 24.2857 |
| | Mint sweet section* | 0.5714 |
| | Mint filter | 0.1714 |
| | Butyl iso valerate 10% menthone SYN | 0.1143 |
| | Isobutyric ald 10% menthone SYN | 0.1143 |
| | Caryophyllene FCC NAT | 0.5714 |
| | Eucalyptol NAT FCC (NF) GCC | 2.2857 |
| | Limonene-L 80 | 1.3714 |
| | Squint NAT | 0.1714 |
| | Pinene alpha NAT | 0.1714 |
| | Pinene beta | 0.1714 |
| | Piperitone NAT | 5.7143 |
| | Terpinene gamma | 0.1143 |
| | Isovaleric ald 10% menthone SYN | 0.1714 |
| | Undecatriene 1% menthone SYN | 0.1429 |
| | Art peppermint top note main | 2.2857 |
| | Menthol SYN USP GCC | 2.8571 |
| | Menthyl-L acetate | 0.5714 |
| | Damascone beta | 0.0286 |
| | Hexenyl trans-2 acetate | 0.1143 |
| | Carvone-L SYN GCC | 8.5714 |
| | Totals | 100.0000 |

| Mint sweet section contains material below | | (% in whole flavor) |
|---|---|---|
| Lactone | Mint lactone | 0.0043 |
| | Hexalactone gamma | 0.0446 |
| Phenolic compound | Vanillin | 0.0006 |
| | Additional Ingredients | 0.5220 |

*

Example 19

A Mint Flavored Toothpaste Formulation J in accordance with the presently disclosed subject matter, e.g., including at least one lactone, as shown in the Table 19, was made. 1.2% of this formulation was used in the test product.

TABLE 19

| | Formulation J ingredients | Weight % |
|---|---|---|
| Lactone | Angelica lactone alpha 98% | 13.3333 |
| Flavor ingredients | Anethol SYN GCC | 5.8333 |
| | Menthol SYN USP GCC | 17.5000 |
| | Peppermint oil, Midwest qual redistilled | 7.0000 |
| | Peppermint oil terpeneless FW NAT | 7.0000 |
| | Artificial peppermint extender* | 14.0000 |
| | Peppermint oil willamette type GCC | 7.0000 |
| | Spearmint oil | 1.6667 |
| | Spearmint oil extender | 0.8333 |
| | Carvone-L SYN GCC | 16.6667 |
| | Piperitone NAT | 8.7500 |
| | Damascone, beta | 0.0833 |
| | Artificial spearmint leaf key | 0.3333 |
| | Totals | 100.0000 |

*Artificial peppermint extender contains material below

| Phenolic compound | Acetyl eugenol | 0.0140 |
|---|---|---|
| | Additional Ingredients | 13.9860 |

Example 20

A Control Flavored Toothpaste Formulation K in accordance with the presently disclosed subject matter, e.g., including at least one lactone, as shown in the Table 20, was made. 1.2% of this formulation was used in the control product.

TABLE 20

| | Formulation K ingredients | Weight % |
|---|---|---|
| Flavor ingredients | Menthol SYN USP GCC | 65.0000 |
| | Menthyl acetate-DL | 2.0000 |
| | Methyl salicylate extra pure | 20.0000 |
| Phenolic compounds | Vanillin | 6.0000 |
| | Ethyl vanillin | 4.5000 |
| Alcohol | Benzyl alcohol | 2.5000 |
| | Totals | 100.0000 |

Example 21

A Raspberry Flavored Mouthrinse Formulation L in accordance with the presently disclosed subject matter, e.g., including at least one lactone and at least one phenolic compound, is shown in Table 21.

TABLE 21

| | Formulation L ingredients | Quantity (kg) | Weight % |
|---|---|---|---|
| Lactone | Undecalactone gamma | 150.0000 | 1.5000 |
| | Angelica lactone alpha 98% | 4000.0000 | 40.0000 |
| | Mint lactone | 10.0000 | 0.1000 |
| Phenolic compounds | Ethyl vanillin | 360.0000 | 3.6000 |
| | Hydroxyphenyl-P(4)-2-Butanone (Raspberry ketone) | 50.0000 | 0.5000 |
| Flavor material | Aldehyde C-16 pure | 200.0000 | 2.0000 |
| | Menthol-L pellets/flakes Synthetic USP (Mint ICC) | 1250.0000 | 12.5000 |
| | Isoamyl acetate | 280.0000 | 2.8000 |
| | Isoamyl butyrate | 650.0000 | 6.5000 |
| | Isoamyl propionate | 350.0000 | 3.5000 |
| | Anisyl acetate | 150.0000 | 1.5000 |
| | Benzyl acetate | 110.0000 | 1.1000 |
| | Benzyl butyrate | 250.0000 | 2.5000 |
| | Benzyl propionate | 400.0000 | 4.0000 |
| | Butyl acetate | 200.0000 | 2.0000 |
| | Ethyl butyrate | 1000.0000 | 10.0000 |
| | Ethyl caproate | 100.0000 | 1.0000 |
| | Ethyl caprylate | 100.0000 | 1.0000 |
| | Ethyl heptanoate | 20.0000 | 0.2000 |
| | Ethyl propionate | 120.0000 | 1.2000 |
| | Styralyl acetate | 250.0000 | 2.5000 |
| | Totals | 10,000.00 | 100.00 |

Example 22

A Vanilla Flavored Mouthrinse Formulation M in accordance with the presently disclosed subject matter, e.g., including at least one lactone and at least one phenolic compound, is shown in Table 22.

TABLE 22

| Formulation M ingredients | | Quantity (kg) | Weight % |
|---|---|---|---|
| Lactone | Decalactone delta | 160.0000 | 1.6000 |
| | Cyclohexyl lactone | 200.0000 | 2.0000 |
| | Angelica lactone Alpha 98% | 4000.0000 | 40.0000 |
| | Natactone dextro 10% Triacetin | 50.0000 | 0.5000 |
| | Octalactone gamma | 50.0000 | 0.5000 |
| Phenolic compounds | Ethyl vanillin | 600.0000 | 6.0000 |
| | Vanillyl alcohol | 480.0000 | 4.8000 |
| Flavor material | Benzaldehyde | 40.0000 | 0.4000 |
| | Heliotropine | 80.0000 | 0.8000 |
| | Butyl butyryl lactate | 80.0000 | 0.8000 |
| | 2-Acetyl pyrazine@ 1% PG | 200.0000 | 2.0000 |
| Solvent | Propylene glycol | 4060.0000 | 40.6000 |
| | Totals | 10,000.00 | 100.00 |

Example 23

A Condensed Milk Lactonic Formulation N in accordance with the presently disclosed subject matter, e.g., including at least one lactone, is shown in the Table 23.

TABLE 23

| Formulation N ingredients | | Quantity (kg) | Weight % |
|---|---|---|---|
| Lactone | Angelica lactone natural | 260.0000 | 26.0000 |
| | Dodecalactone delta natural | 250.0000 | 25.0000 |
| | Decalactone delta natural | 100.0000 | 10.0000 |
| Flavor material | Sulfurol Natural | 40.0000 | 4.0000 |
| Solvent | Propylene glycol | 350.0000 | 35.0000 |
| | Totals | 10,000.00 | 100.00 |

Example 24

A Flavored Mouthwash Formulation O in accordance with the presently disclosed subject matter, e.g., including at least one lactone and at least one phenolic compounds, as shown in the Table 24, was made.

TABLE 24

| Mouthwash base formulation | Weight % |
|---|---|
| Alcohol | 18.2 |
| Non-ionic surfactant | 0.2453 |
| Flavor (control or test flavor)* | 0.3049 |
| Buffer | 0.1176 |
| Artificial sweetener | 19.7418 |
| Food preservative | 0.0347 |
| Color | 0.05 |
| DI water | 61.3057 |
| Totals | 100 |

TABLE 25

| Control flavor formulation | Weight % |
|---|---|
| Flavor oils | 100 |
| Totals | 100 |

TABLE 26

| Test flavor formulation | | Weight % |
|---|---|---|
| Lactone | Angelica lactone-Alpha 98% | 8.14042 |
| Flavor material | Piperitone NAT | 7.63165 |
| | Damascone, Beta | 0.05088 |
| | Hexenyl-Trans-2 Acetate | 0.20351 |
| | Artificial Peppermint Extender* | 4.3246 |
| | Carvone - L SYN GCC | 5.08776 |
| | Flavor Oils | 74.56113 |
| | Totals | 99.9999 |
| *Artificial Peppermint Extender contains materials below | | |
| Lactone | Cyclohexyl lactone | 0.00031 |
| | Mint lactone | 0.00031 |
| Phenolic compounds | eugenol acetate | 0.00432 |
| | Thymol | 0.00019 |
| | Vanillin | 1.7E−05 |
| | Additional ingredients | 4.3194 |

Example 25

A Flavored Gum Formulation P in accordance with the presently disclosed subject matter, e.g., including at least one lactone and at least one phenolic compound, as shown in the Table 27, was made. The flavor formulation was added to a gum base containing sorbitol, xylitol, mannitol, soya lecithin, glycerin, triacetin, acesulfame K, and aspartame.

TABLE 27

| Formulation P ingredients 3.15% in product (spray dry 3%, liquid 0.15%) | | Weight % |
|---|---|---|
| Spray dry | Starch Modified Capsul (Non-GM IP) SYN | 6.6667 |
| | Malto dextrin DE-10 NAT | 23.3333 |
| | Hydroxypropyl Methyl Cellulose | 0.4762 |
| | Water city NAA | 57.1429 |
| | Angelica lactone-Alpha 98% | 3.0476 |
| | Carvone - L SYN GCC | 2.2857 |
| | Artificial Peppermint Extender* | 0.7619 |
| | Piperitone NAT | 1.5238 |
| Liquid flavor | Spearmint oil | 2.3810 |
| | Spearmint oil extender | 1.4286 |
| | Carvone - L SYN GCC | 0.7143 |
| | Damascone, Beta | 0.0476 |
| | Artificial spearmint leaf key | 0.1905 |
| | Totals | 100.0000 |
| *Artificial Peppermint Extender contains materials below % in whole flavor | | |
| Lactones | Cyclohexyl lactone | 0.0001 |
| | Mint lactone | 0.0001 |
| Phenolic compounds | Acetyl eugenol | 0.0008 |
| | Thymol | 0.000034 |
| | Vanillin | 0.000003 |

Example 26

Example 26 is a clinical study performed to test whether the breath mint tablets of Formulations G-1 have a positive effect against food derived malodors (e.g., fresh garlic and pepperoni) and bacteria derived malodors (e.g., methyl mercaptan and allyl mercaptan). Methyl mercaptan and allyl mercaptan are also found in malodor producing food products. A brand peppermint breath tablet and unflavored placebo base products were tested as controls.

Twenty experienced panelists were instructed on sniffing and scoring the intensity of the malodor compounds specified in Table 28. Sniff jars containing malodor materials were given to the panelists. The panelists sniffed and scored the malodor samples following the Malodor Score Chart Table 30.

The malodor control samples were prepared as listed in Table 28. In particular, 0.10% methyl mercaptan was dissolved in ethyl alcohol 95% natural. A 100 ppm solution of methyl mercaptan in distilled water (DW) was prepared for the test, and 100 µL was added into each sniff jar. 0.10% allyl mercaptan was dissolved in ethyl alcohol 95% natural. A 10 ppm solution of allyl mercaptan in DW was prepared for the test, and 100 µL was added into each sniff jar. Ten grams of chopped fresh garlic was blended in 100 grams of DW. The garlic and water solution was filtered. A 10% garlic solution in DW was prepared for the test, and 1 mL was added into each sniff jar. Pepperoni was chopped, and 0.5 grams was added into each sniff jar.

The test samples were prepared as indicated in Table 29. In particular, the brand peppermint breath tablet was prepared by grinding one tablet (1.8 g) into a powder and then mixing it with 1.8 mL of DW to make a slurry. Formulations G-I flavored product samples (i.e., spearmint, peppermint, and coolmint, respectively) were prepared by grinding one tablet (1.8 g) into a powder and then mixing it with 1.8 mL of DW to make a slurry. 1.8 g of the placebo sample (the base of the breath mint tablets without flavor added) was mixed in DW to make a slurry.

TABLE 28

Malodors Samples

| 1 | Allyl Mercaptan 10 ppm D.W. | 100 µL |
| 2 | Methyl Mercaptan 100 ppm D.W. | 100 µL |
| 3 | Fresh Garlic 10.0% solution D.W. | 1 mL |
| 4 | Pepperoni Dry | ½ gram |

TABLE 29

Experimental Setup

| A | Placebo Control Tablet | 1 tablet + 1.8 mL D.W. + (1, 2, 3, or 4 from Table 28) |
| B | Control Peppermint Tablet | 1 tablet + 1.8 mL D.W. + (1, 2, 3, or 4 from Table 28) |
| C | Formulation G Spearmint Tablet | 1 tablet + 1.8 mL D.W. + (1, 2, 3, or 4 from Table 28) |
| D | Formulation H Peppermint Tablet | 1 tablet + 1.8 mL D.W. + (1, 2, 3, or 4 from Table 28) |
| E | Formulation I Cool Mint Tablet | 1 tablet + 1.8 mL D.W. + (1, 2, 3, or 4 from Table 28) |

The panelists were instructed to sniff the 20 test samples that were presented blind coded and visually blinded (to prevent influence) and rank the results according to Table 30. The samples were randomized within their odor groups. After each odor assessment, the panelists were instructed to sniff a small jar of baking soda to clear their airways of any lingering odors before the next assessment. The 20 assessments were completed in one session lasting between 10 and 15 minutes.

TABLE 30

Malodor Score Chart

| score | description |
|---|---|
| 5 | extreme malodor |
| 4 | strong malodor |
| 3 | moderate malodor |
| 2 | slight malodor |
| 1 | barely detectable malodor |
| 0 | no malodor |

TABLE 31

Summary of Results

| | | A Placebo Control | B Peppermint Control | C Form. G Spearmint | D Form. H Peppermint | E Form. I Cool Mint |
|---|---|---|---|---|---|---|
| 1 | Allyl Mercaptan | 3.5 A | 1.9 B | 1.0 C | 1.7 CB | 1.8 CB |
| 2 | Methyl Mercaptan | 3.3 A | 2.0 B | 1.6 B | 1.6 B | 1.5 B |
| 3 | Fresh Garlic | 4.9 A | 3.8 CB | 3.2 C | 3.7 CB | 4.0 B |
| 4 | Pepperoni | 3.2 A | 2.2 B | 1.6 B | 2.2 B | 1.9 B |

*Means with the same letter are not significantly different ($p < 0.05$).

According to the results (Table 31), the flavored control product and Formulations G-I displayed a statistically significant reduction in malodor as compared with the placebo control Formulations G-I breath mints are effective at reducing the malodor scores with all of the malodor reference samples. Formulation G breath mint revealed a better performance in malodor reduction with all of the malodor references except for methyl mercaptan, where it performed better that the peppermint control and almost as well as the cool mint breath mint. Formulation H breath mint performed equally well, if not better, than the peppermint control and better than the cool mint breath mint with respect to the allyl mercaptan and garlic malodors.

The cool mint tablet performs equivalent to or better than the Formulation H breath mint. The results are attributed at least in part to higher flavor levels and potentially better release of flavor from the slurry powder base itself.

Example 27

In Example 27, a clinical study was performed to test the effects of the toothpaste of Formulation J on oral malodor. In particular, the study compared the oral malodor/breath protection efficacy of a the Mint Toothpaste of Formulation J relative to negative controls using hedonic breath assessment. This was a randomized, parallel, double-blinded clinical trial with approximately 45 adult volunteers with oral malodor of at least 7.0±0.5 on the nine point hedonic scale. At Baseline, subjects underwent a hedonic breath evaluation conducted by qualified odor judges, and the 45 subjects that meet the continuance criteria were randomly assigned to one of three treatments (15/group) at Product Distribution. The three treatments were: 1) the toothpaste of Formulation J; 2) brand mint toothpaste; and 3) control winter mint flavored toothpaste (Formulation K). The control products and the Formulation J product had approximately a 1.2% flavor dose.

Subjects were disqualified after the baseline evaluation if their breath odor did not meet the minimum requirement of at least 7.0±0.5 on the hedonic scale, or they had an odor of systemic origin which would interfere with the study. Subjects were also disqualified if they had less than 20 natural teeth.

Subjects were instructed to use the test product in the morning and evening before the Assessment Day. The subjects were instructed to abstain from ingesting food or drinks, as well as, refrain from using oral hygiene products on the morning of the malodor evaluation on Assessment Day. The subjects were also requested not to use tobacco products, body lotions, shampoo, perfume, or lipstick prior to the oral malodor evaluation. The subjects were not allowed to brush their tongue for the duration of the study, and they had to delay any elective dentistry. Only subjects that abided by these requests were evaluated. The subjects also underwent a wash out period which required them all to use the same standard toothpaste for a week leading up to the day before the experiment.

On Assessment Day, subjects were evaluated for overnight hedonic malodor by trained judges. Next they were supervised while brushing with the product for 60 seconds. Malodor evaluations were taken by the judges immediately after use, 30 minutes after use, 1 hour after use, 2 hours after use, and 4 hours after use. A panel of trained odor judges were used for each of the test sessions using a nine point hedonic scale was used: 1) most pleasant; 2) very pleasant; 3) moderately pleasant; 4) slightly pleasant; 5) neither pleasant nor unpleasant; 6) slightly unpleasant; 7) moderately unpleasant; 6) very unpleasant; and 9) most unpleasant. In order to create a reproducible assessment, subjects were instructed to close their mouth and breathe through their nose for two minutes. After two minutes the subjects were instructed to count out loud from 1-20 while the judges assessed the odor intensity at approximately 10 centimeters from the subject's mouth.

The results of the malodor hedonic scale study is provided in FIG. 1. The data demonstrated that overtime the brand mint and Formulation J samples exhibited either a directional trend or significant improvement in malodor reduction over the winter mint flavored control (Formulation K). By 2 and 4 hours, the toothpaste of Formulation J performed better than the winter mint flavored control.

Example 28

In Example 28, a clinical study was performed to test the effects of the mouthwash of Formulation O relative to a negative control using hedonic breath assessment. This was a randomized, parallel, double-blinded clinical trial with approximately 45 adult volunteers with oral malodor of at least 7.0±0.5 on the nine point hedonic scale. At Baseline, subjects underwent a hedonic breath evaluation conducted by qualified odor judges, and the 45 subjects that meet the continuance criteria were randomly assigned to one of three treatments (15/group) at Product Distribution. The three treatments were: 1) the Test Mouthwash of Formulation 0; 2) control mouthwash (Example 24); and 3) water.

Subjects were instructed to use the same standard toothpaste and toothbrush for one week prior to the evaluation days (i.e., a wash out period). The subjects were also requested not to use tobacco products, body lotions, shampoo, perfume, or lipstick prior to the oral malodor evaluation. The subjects were also not allowed to brush their tongue for the duration of the study, and they were asked to delay any elective dentistry. The subjects were also asked to refrain from spicy food, e.g. Mexican and Indian food, and heavy garlic 24 hours prior to breath assessment on evaluation days.

On Assessment Day, subjects were evaluated for overnight hedonic malodor by three trained judges. Next the subjects were randomly allocated a test or control mouthwash, and supervised use of the mouthwash was performed for 30 seconds with 20 ml. After product use, the subjects underwent further hedonic malodor evaluations at the following time points: immediately after use, 30 minutes after use, 1 hour after use, 2 hours after use, 4 hours after use. A panel of three trained odor judges were used for each of the test sessions using a nine point hedonic scale was used: 1) most pleasant; 2) very pleasant; 3) moderately pleasant; 4) slightly pleasant; 5) neither pleasant nor unpleasant; 6) slightly unpleasant; 7) moderately unpleasant; 6) very unpleasant; and 9) most unpleasant. In order to create a reproducible assessment, subjects were instructed to close their mouth and breathe through their nose for two minutes. After two minutes the subjects were instructed to count out loud from 1-20 while the judges assessed the odor intensity at approximately 10 centimeters from the subject's mouth.

Figure 2:
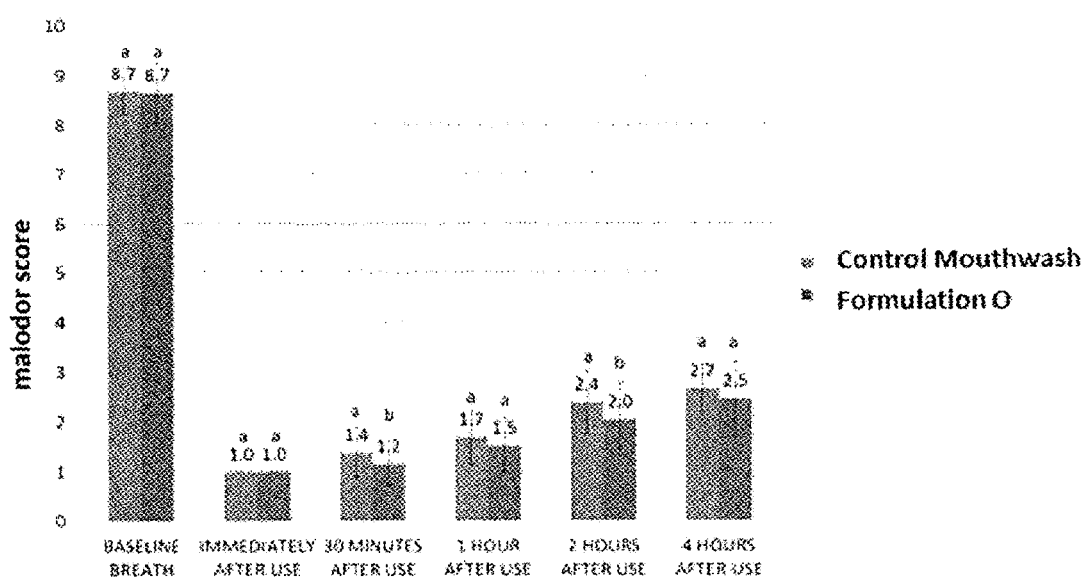
FIG. 2: Hedonic scale results from the clinical study evaluating the mouthwash of Formulation O. Statistics were run between each treatment group at each time point. Bars with the same letter are less than 95% significance.

The results of the malodor hedonic scale study is provided in FIG. 2. The results showed 95% significance at 30 minutes and 2 hours and a very strong directional difference at 1 hour and 4 hours. This trend was consistent through all time points with the mouthwash of Formulation O performing better.

The present presently disclosed subject matter is not to be limited in scope by the specific embodiments described herein. Indeed, various modifications of the presently disclosed subject matter in addition to those described herein will become apparent to those skilled in the art from the foregoing description and the accompanying figures. Such modifications are intended to fall within the scope of the appended claims.

Patents, patent applications publications product descriptions, and protocols are cited throughout this application the disclosures of which are hereby incorporated herein by reference in their entireties for all purposes.

What is claimed is:

1. A malodor eliminating composition, comprising at least one lactone and at least one phenolic compound, and at least one solvent;
    wherein the total amount of lactone is present in an amount of from about 20% w/w to about 50% w/w of the total malodor elimination composition;
    wherein the at least one lactone is a monocyclic 5-membered lactone ring with one unsaturated bond;
    wherein the at least one phenolic compound is selected from the group consisting of eugenol, vanillyl butyl ether, vanillyl ethyl ether, benzyl salicylate, methyl salicylate, raspberry ketone, thymol, vanillin, ethyl vanillin, vanitrope, and mixtures thereof;
    wherein the total amount of phenolic compound is present in an amount of from about 20% w/w to about 50% w/w of the total malodor elimination composition; and
    wherein the at least one solvent is selected from the group consisting of benzyl alcohol, 3-(1-menthoxy)propane-1,2-diol, p-menthane-3,8-diol, propylene glycol, diethylene glycol, dipropylene glycol, triacetine (glycerine triacetate) medium chain triglyceride, and mixtures thereof.

2. The malodor eliminating composition of claim 1, wherein the at least one lactone is selected from the group consisting of *angelica* lactone alpha, *angelica* lactone beta, 2(5H) furanone, and mixtures thereof.

3. The malodor eliminating composition of claim 1, further comprising a malodor masking compound.

4. The malodor eliminating composition of claim 3, wherein the malodor masking compound is selected from the group consisting of menthol, anisyl acetate, ethyl acetate, phenethyl alcohol, ethyl 2-methyl butyrate, ethyl butyrate, propylene glycol, citrus oils, peppermint oil, spearmint oil, oil of wintergreen, cinnamon, and ginger.

5. An end product comprising the malodor eliminating composition of claim 1.

6. The end product of claim 5, wherein the end product includes an oral care product, a beverage, a food product, or a fragrance containing product.

7. The end product of claim 6, wherein the oral care product includes toothpaste, mouthrinse, breath mint, dental floss, or gum.

8. The end product of claim 6, wherein the fragrance containing product includes a deodorizer product, a cleaning product, a personal care product, or an animal care product.

9. The end product of claim 8, wherein the personal care product includes shampoo, rinse, rinse-in-shampoo, hair conditioner, hair treatment, hair pack, hairspray, dry shampoos, bath soap, perfume soap, clear soap, synthetic soap; body soap, body shampoo, hand soap, bath salt, bath tablet, foam bath, milk bath, bath jelly, or bath cube.

10. The end product of claim 8, wherein the cleaning product includes detergents for clothes, liquid laundry detergent, laundry soap, compact detergent, all-purpose detergents, softener, household cleaners, house wash, toilet cleaner, bath cleaner, glass cleaner, fungicide, cleaner for drain pipe, kitchen soap, kitchen synthetic soap, dish wash detergents, beaching agents, oxidant bleach, reductive bleach, optical bleach, spray aerosols, powder spray, deodorant-aromatics, aromatics, car fresheners, room fresheners, candles, or carpet deodorizers.

11. The end product of claim 8, wherein the animal care product includes shampoos, bath powders, dry shampoos, cleaning cloths, deodorizing sprays, pet bedding deodorant, pet tooth pastes, chew toys, pet food, pet treats, cat litter, or cat litter box deodorants.

* * * * *